(12) United States Patent
Berka et al.

(10) Patent No.: US 6,893,839 B1
(45) Date of Patent: May 17, 2005

(54) METHODS FOR PRODUCING POLYPEPTIDES IN CYCLOHEXADEPSIPEPTIDE-DEFICIENT CELLS

(75) Inventors: Randy M. Berka, Davis, CA (US); Michael W. Rey, Davis, CA (US); Wendy T. Yoder, Winters, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/482,788

(22) Filed: Jan. 13, 2000

Related U.S. Application Data

(63) Continuation-in-part of application No. 09/229,862, filed on Jan. 13, 1999, now abandoned.

(51) Int. Cl.⁷ .......................... C12N 1/16; C12N 15/00; C12P 21/06; C07H 21/04; C07K 17/00
(52) U.S. Cl. .................. 435/69.1; 435/254.7; 435/71.1; 435/440; 435/254.11; 435/69.4; 435/183; 435/189; 435/193; 435/185; 435/232; 530/350; 536/23.2
(58) Field of Search ............................... 435/69.1, 71.1, 435/440, 254.7, 254.11, 69.4, 183, 189, 193, 195, 232; 530/350; 536/23.2

(56) References Cited

PUBLICATIONS

Witkowski et al., Biochemistry 38:11643–11650, 1990.*
Seffernick et al., J. Bacteriol. 183(8):2405–2410, 2001.*
Bork, Genome Research, 10:398–400, 2000.*
Tsuchiya et al., Appl. Microbiol. Biotechnol. 40:327–332, 1993.*
Broun et al., Science 282:1315–1317, 1998.*
Van de Loo et al., Proc. Natl. Acad. Sci. 92:6743–6747, 1995.*
Shemyakin et al., 1969, Journal of Membrane Biology 1: 402–430.
Reper et al., 1995, European Journal of Biochemistry 230: 119–126.
Grove and Pople, 1980, Mycopathologia 70: 103–105.
Haese et al., 1993, Molecular Microbiology 7: 905–914.
Herrmann et al., 1996, Molecular Plant–Microbe Interactions 9: 226–232.

* cited by examiner

*Primary Examiner*—Rebecca E. Prouty
*Assistant Examiner*—Delia M. Ramirez
(74) *Attorney, Agent, or Firm*—Robert L. Starnes

(57) ABSTRACT

The present invention relates to methods for producing a heterologous polypeptide, comprising: (a) cultivating a mutant of a parent filamentous fungal cell under conditions conducive for the production of the heterologous polypeptide, wherein (i) the mutant cell comprises a nucleic acid sequence encoding the heterologous polypeptide and (ii) the mutant produces less of the cyclohexadepsipeptide than the parent filamentous fungal cell when cultured under the same conditions; and (b) isolating the heterologous polypeptide from the cultivation medium. The present invention also relates to mutants of filamentous fungal cells and methods for obtaining the mutant cells. The present invention also relates to isolated cyclohexadepsipeptide synthetases and isolated nucleic acid sequences encoding the cyclohexadepsipeptide synthetases. The present invention also relates to nucleic acid constructs, vectors, and host cells comprising the nucleic acid sequences as well as methods for producing the cyclohexadepsipeptide synthetases. The present invention further relates to cyclohexadepsipeptides produced by the cyclohexadepsipeptide synthetases.

29 Claims, 10 Drawing Sheets

```
AATTAGATTCCACTAGTACGCCATTGTAGAATCAAGGCCAAGATATGAACAACCCATAAGTAACGGCGATCCTGTCTCAT    80
GTATCCAAAATAAGAGACACGGCATATTCACTGCTTTGCAGATTCTTTCAAATCTCCCCTGGTACTTCTCGAGAAGCTACTGGA  160
TGAATGAGTCTCTTGGCTCAGATTAGATATATTCACTGTATCTGCCGAATAGACTTTGCCTGGTAGCATTAACGTTCCTA  240
TATTCTATTATCAAATCCTTACATTCAATATGGAATTCAATAGTCCTGTCTGATGGTAGGCAAGACCCTGCCACCTACACCA  320
                                  M  E  Y  L  T  A  V  D  G  R  Q  D  L  P  P  T  P
GCTTCGTTTGTAGTCATGGAGATAGTCCCCTCAATAGCTCTTACGAGCAACTCTTCCATCTCTATGGTCTGGATTCGAG  400
 A  S  F  C  S  H  G  D  S  P  L  N  S  S  Y  E  Q  L  F  H  L  Y  G  L  D  S  S
TCGCATCGAAGCTATCAAACCATGCACACCTTTCCAGCTGCAATGATCGACTGCTTTGGATAAGCAGTCTGCTA  480
 R  I  E  A  I  K  P  C  T  P  F  Q  L  D  M  I  D  C  N  A  L  D  K  Q  S  A
TCGGCCATGCGGTGTATGATGTCCCAACGACATTCTCGTTTGCGCCTTGCGGTGAAGGAGATCGTCAACCAA  560
 I  G  H  A  V  Y  D  V  P  T  D  I  D  I  S  R  F  A  L  A  W  K  E  I  V  N  Q
ACCCCAGCCTTGCGAGCCTTTGCTGGTCTTCTTCAAGTCTCAAGTCATCTCTAAAAGATAGTTTGTCTT  640
 T  P  A  L  R  A  F  A  F  T  S  D  S  G  K  T  S  Q  V  I  L  K  D  S  F  V  F
CTCATGGATGTGCTGGTCTTCTTCGAGCTCCCCAGATGAAGCTGGTTCGGGATGAAGCTGCTGCATCCGGCCAC  720
 S  W  M  C  W  S  S  S  S  P  D  E  V  V  R  D  E  A  A  A  A  S  G  P
GCTGCAACCGCTTCGTTCTACTTGAAGACATGCAGACGAAGAAATGTCAGCTGGTTTGGACCTTCAGTCATGCATTGGTA  800
 R  C  N  R  F  V  L  L  E  D  M  Q  T  K  K  C  Q  L  V  W  T  F  S  H  A  L  V
GACTGCACTTTCCAACAACGCGTCCTGAGCCGTGTTTTCGCGGCTTACAAGCATGAGAAGGACACACATCGGCTGAGAC  880
 D  V  T  F  Q  Q  R  V  L  S  R  V  F  A  A  Y  K  H  E  K  D  T  H  R  P  E  T
ACCCGAGTCATCTGATGCCACTCTGACTCTCCAGTCAGTCTCCGTGTCCATGCTGTCCATGCTGCGAGGACAATGCCGTAT  960
 P  E  S  S  D  A  T  D  T  D  S  Q  S  V  S  V  S  M  S  C  E  D  N  A  V
CGGGCGACTCATTTCTGGCAAACTCACTTGACGATCTCAATGCTGTCCTCCCCGTCTTCCCCACCTGATGGTG  1040
 S  A  T  H  F  W  Q  T  H  L  N  D  L  N  A  S  V  F  P  H  L  S  D  H  L  M  V
CCCAACCCAACTACAACAGCAGAGCATCGTATCACATTCTCTTCACAGAAAGCACTATCCAATTCTGCCATCTGCCG  1120
 P  N  P  T  T  A  E  H  R  I  T  F  P  L  S  Q  K  A  L  S  N  S  A  I  C  R
TACTGCACTCTCAATACTCCTCGCGACTACACTCCTCTGACGAGGCCTTGTTTGGTGCGGTAACTGAGCAATCTCTAC  1200
 T  A  L  S  I  L  L  S  R  Y  T  H  S  D  E  A  L  F  G  A  V  T  E  Q  S  L
CATTTGACAAACACTATCTTGCAGATGGTACGTACCAAACAGTTGCACCCCTTCGTGTACGCCAATCAAATCTTCGT  1280
 P  F  D  K  H  Y  L  A  D  G  T  Y  Q  T  V  A  P  L  R  V  H  C  Q  S  N  L  R
```

Fig. 1A

```
GCATCAGAGATGTCATGGATGCAATCTCTTCTTACGATGATGCCTTGGTCATCTCGCCCCATTTGGCTTTTGGGCTTCGACATCCG  1360
 A  S  D  V  M  D  A  I  S  S  Y  D  D  R  L  G  H  L  A  P  F  G  L  R  D  I  R
CAACACTGGTGATAATGGCTCTGCCAACAGATAACAGATTCCAAACTGTTTTACTCGTCACCGATGGCAGCCACGTAAACAATG  1440
 N  T  G  D  N  G  S  A  A  C  D  F  Q  T  V  L  V  T  D  G  S  H  V  N  N
GTATCAACGGTTTCCTCCAACAGATAACAGAGTCAAGCCATTTCATGCCGTGCCCTTCTGCACTGT  1520
 G  I  N  G  F  L  Q  Q  I  T  E  S  S  H  F  M  P  C  N  N  R  A  L  L  L  H  C
CAGATGGAAAGTAGCGGGAGCTCTGCTGTTGCCACCACAATGTTATCGATTCGCTTCAGACAACGCGTCTGCT  1600
 Q  M  E  S  S  G  A  L  L  V  A  Y  Y  D  H  N  V  I  D  S  L  Q  T  T  R  L  L
ACAGCAGTTTGGTCATCGATCAAGTGTTTGCAAAGTCCTCCGAGCTCTATGGCTGAGGTCAACTTGATGACTG  1680
 Q  Q  F  G  H  L  I  K  C  L  Q  S  P  L  D  L  S  S  M  A  E  V  N  L  M  T
AGTATGACAGAGCAGAGATTGAGAGTTGGAACTCGCAACCGTTAGAGGTACAGGATACCCTGATCCACCATGAGATGTTG  1760
 E  Y  D  R  A  E  I  E  S  W  N  S  Q  P  L  E  V  Q  D  T  L  I  H  H  E  M  L
AAAGCTGTTTCTCATTCCCCACCAAAACGGCCATCCAAGTCGTGGGATGGAGACTCGAGCTCGACAATGT  1840
 K  A  V  S  H  S  P  T  K  T  A  I  Q  A  W  D  G  D  W  T  Y  S  E  L  D  N  V
TTCGTCAAGACTGGTCATTGCTTCAATGCTCTGGCTGTGTTCTCAAGTCTGGTAATGCTTCACTCTAATTGATCCCACCA  1920
 S  S  R  L  A  V  H  I  K  S  L  G  L  R  A  Q  Q  A  I  I  P  V  Y  F  E  K
CGAAATGGGTCATTGCTTCAATGCTCTGGCTGTGTTCTCAAGTCTGGTAATGCTTCACTCTAATTGATCCCAATGATCCACCA  2000
 S  K  W  V  I  A  S  M  L  A  V  L  K  S  G  N  A  F  T  L  I  D  P  N  D  P  P
GCTCGAACTGCCCAGTCGTCACGCAGAGACTCGGGCGCTTACTTCCAAGCTGTAGCGACGAGCTTCTGCAATCAGTTCTGCCAAGCTTCCAAGACGATTTCTCAAGTCTGACCA  2080
 A  R  T  A  Q  V  V  T  Q  T  R  A  T  V  A  L  T  S  K  L  H  R  E  T  V  Q  K
GCTTGTAGGCCGTTGCGTTGGTGTTGTGATGACGAGCTTGATGACGAGCTTCACTTCGGTCTTCTGGTAGCACGGGCGACCCGAAAGGCATCATGATTGAACACCGAGCG  2240
 L  V  G  R  C  V  V  D  D  E  L  L  Q  S  V  S  A  S  D  D  F  S  S  L  T
AATCGCAAGACTTGGCCTGACGTGATCTTCACTTCGGTCTCTTGGTAGCACGGGCGACCCGAAAGGCATCATGATTGAACACCGAGCG  2240
 K  S  Q  D  L  A  Y  V  I  F  T  S  G  S  T  G  D  P  K  G  I  M  I  E  H  R  A
TTCTCATCATGTGCACTCAAGTCACTCAAGTTCGGCGCGTCTCTTGGCATCAACTCGTGCCCTACAATTTGGAACCCATGC  2320
 F  S  S  C  A  L  K  F  G  A  S  L  G  I  N  S  D  T  R  A  L  Q  F  G  T  H  A
CTTTGGCGCATGTCTTCTGAGATTATGACTACTCTCATCAACGGTGGCGTTTGTATTCCCCGACGATGATCGTA  2400
 F  G  A  C  L  L  E  I  M  T  T  L  I  N  G  G  C  V  C  I  P  S  D  D  D  R
TGAACAGTATCCCGTCCTTCATCAACCGATACAACGTTAATTGATACATGGATGATGGCGACACCTTCGTACATGGGAACCTTTTCA  2480
 M  N  S  I  P  S  F  I  N  R  Y  N  V  N  W  M  M  A  T  P  S  Y  M  G  T  F  S
```

Fig. 1B

```
CCTGAAGAGCGTTCCTGCCCTTGCGACATTGGTACTTGTTGGGGAGCAGATGTCATCTTCAGTCAACGCAATCTGGCCCC  2560
 P  E  D  V  P  G  L  A  T  L  V  G  E  Q  M  S  S  S  V  N  A  I  W  A  P
CAAGCTCCAACTCTTGAACGGTACGGGACAGAGTGAAAGTTCCTCAATTTGTTTGCCTCCAATATGTCAACTGAGCCCA  2640
 K  L  Q  L  L  N  G  Y  G  Q  S  E  S  S  S  I  C  F  A  S  N  M  S  T  E  P
ACAACATGGGCAGAGCAGTCGGAGCTCATTCATTGACCCGACGATATAAACGACTAGTTCCGATTGGAGCT  2720
 N  N  M  G  R  A  V  G  A  H  S  W  V  I  D  P  N  D  I  N  R  L  V  P  I  G  A
GTGGGAGAACTGGTCATTGAGAGTCCAGGCATTGCCCGCGACTACATTGTTCCCCCCCCTCCGGAGAAGTCCCCATTCTT  2800
 V  G  E  L  V  I  E  S  P  G  I  A  R  D  Y  I  V  P  P  P  E  K  S  P  F  F
CACAGACATTCCAAGCTGGTATCCAGCGAACACGTTTCCTGATGGGCAAAACTCTACAGGACAGAGATCTTGCAAGAT  2880
 T  D  I  P  S  W  Y  P  A  N  T  F  P  D  G  A  K  L  Y  R  T  G  D  L  A  R
ATGCCTCCGATGGGGTCCATCGTTTGCCTTGGGCCATAGACTCGCAGGTCAAGATCCGGGACAGCGTGTTGAGCTGGGT  2960
 Y  A  S  D  G  S  I  V  C  L  G  R  I  D  S  Q  V  K  I  R  G  Q  R  V  E  L  G
GCCATTGAGACCCATCTCCGACAGCAGATGCCAGATGACTTGACTATTGTGGTAGAAGCTACCAAGCGATCCCAATCTGC  3040
 A  I  E  T  H  L  R  Q  Q  M  P  D  D  L  T  I  V  V  E  A  T  K  R  S  Q  S  A
CAACAGCACACATCCTTAATTGCATTCCTAATAGGGTCTCTTTACTTCGGAAATAGACCCTCGGATGCCCACATTCTGGACC  3120
 N  S  T  S  L  I  A  F  L  L  I  G  S  S  Y  F  G  N  R  P  S  D  A  H  I  L  D
ATGGAGCTACCAAAGCTATCAACATAAAGCTAGCAGTATGCCTCGACACTCTATCCCTCATTCTACATCTGCATG  3200
 H  D  A  T  K  A  I  N  I  K  L  E  Q  V  L  P  R  H  S  I  P  S  F  Y  I  C  M
CTGGAGCTTCCACGTACTGCCACGGGAAGATACATGGGCAAAGACATCTTGGACAAGCA  3280
 L  E  L  P  R  T  A  T  G  K  I  D  R  R  I  M  G  K  D  I  L  D  K  Q
GACCCAAGGGCCATTGTTCAACAAGCCCGGCCACGGCCAGCCAGCCAACTTCTTCGAGACAGCTCCACAGTATCT  3360
 T  Q  G  A  I  V  Q  Q  A  P  A  P  I  P  V  F  A  D  T  A  A  K  L  H  S  I
GGGTACAGAGTTTGGGTATCGATCCAGCCGCCGAGGTCCGTTGGTATGGACCTCAAGGTCTCTAACATCTACCAGCCTTGC  3440
 W  V  Q  S  L  G  I  D  P  A  T  V  N  V  G  A  T  F  F  E  L  G  G  N  S  I  T
GCTATCAAGATGGTGAACATGGCGAGGTCCGTTGGTATGGACCTCAAGGTCAAGTCAACTCTCTACACTCTCTACACT
 A  I  K  M  V  N  M  A  R  S  V  G  M  D  L  K  V  S  N  I  Y  Q  H  P  T  L  A
GGGAATTCCGCGGTCGTCAAGGGTGATCCTCCTCAAGTCAACTCATGAGGGACCTGTTGAGC  3600
 G  I  S  A  V  V  K  G  D  P  L  S  Y  T  L  I  P  K  S  T  H  E  G  P  V  E
AGTCTTATTCACAAGGCCGACTATGGTTCCTGATCAGTTGGCAGTTGGATCTGTGGTATCTGATTCTGATTCCATATGCTGTG  3680
 Q  S  Y  S  Q  G  R  L  W  F  L  D  Q  L  D  V  G  S  L  W  Y  L  I  P  Y  A  V
```

Fig. 1C

```
AGAATGCGCGGGCCTGTCAATGTCGACGTCGGGCTCTTGCAGCGCTTGAACAGCGACACGAGACTCTTAGAAC   3760
 R  M  R  G  P  V  N  V  D  A  L  R  R  A  L  A  A  L  E  Q  R  H  E  T  L  R  T
GACATTTGAAGACCAGGATGGTCGGTGTACAAATTGTTCACGAGAAGCTTTCTGAGGAGATGAAGTCATTGATCTCT  3840
 T  F  E  D  Q  D  G  V  V  Q  I  V  H  E  K  L  S  E  E  M  K  V  I  D  L
GTGGTTCAGACCTTGACCCGTTTGAGGTGTTGAACCAAGAACAGACTACTCCCTTCAATCTCTCATCTGAAGCTGGCTGG  3920
 C  G  S  D  L  D  P  F  E  V  L  N  Q  E  Q  T  T  P  F  N  L  S  S  E  A  G  W
AGAGCGACGCTCTTACGACTTGGTGAAGATGACCACATCCTCACTATTGTCATGCATCATCTCAGATGTTGGTC  4000
 R  A  T  L  L  R  L  G  E  D  D  H  I  L  T  I  V  M  H  H  I  S  D  G  W  S
AATTGATGTCTTGCGACGCGATCTCAATCAGCTCTACTCAGCTGCGCTCAAGGACTCAAAGACCCGCTGTCAGCACTCA  4080
 I  D  V  L  R  R  D  L  N  Q  L  Y  S  A  L  K  D  S  K  D  P  L  S  A  L
CTCCTCTACCTATCCAGTACAGCGACTTTGCAAAATGGCAGAAGCAGGAGAAGCAACTCAACTAC   4160
 L  L  Y  P  I  Q  Y  S  D  F  A  K  W  Q  K  Q  E  K  Q  L  N  Y
TGGAAGAAGCAACTCAAAGACTCTTCCCCAGCAAAGATCCCGACTCTGTCTGGAGACGC   4240
 W  K  K  Q  L  K  D  S  S  P  A  K  I  P  T  D  F  A  R  P  A  L  L  S  G  D  A
AGGTTGCGTACATGTTACCACGACGAGCTCTGCAACGACAACACGACTCTT   4320
 G  C  V  H  V  T  I  D  G  E  L  Y  Q  S  L  R  A  F  C  N  E  H  N  T  S
TCGTCGTTCTTCTAGCTGCGTTCCGTGAAGACGCTGTCATTGGTACACCAATT   4400
 F  V  V  L  L  A  A  F  R  A  A  H  Y  R  L  T  A  V  E  D  A  V  I  G  T  P  I
GCGAATCGCAACCTGAACTGGAGGATATCATCGGCTGCTTTGTCAATACGCAGTGTATGCGAATCAACATAGATCA   4480
 A  N  R  N  R  P  E  L  E  D  I  I  G  C  F  V  N  T  Q  C  M  R  I  N  I  D  H
TCACGATACCTTTGGGACTTTGATCAACCAAGTCAAGAGATCTGTCAAGCACCTCTGCCACAACTCATTTTGCAGTGCAC   4560
 H  D  T  F  G  T  L  I  N  Q  V  K  A  T  T  A  A  F  E  N  E  D  I  P  F
AGCGCGTTGTATCAGCACTACAGCCTGGATCCAGAGATCTGTCCAGGGTCTCGAGTTCCGGTCTCGAGTCCGTGCCTAGCCAAAGCGTACACTCGATTGA  4720
 E  R  V  S  A  L  Q  P  G  S  R  D  L  S  S  T  P  L  A  Q  L  I  F  A  V  H
TCACAAGGACCTTGGAAGATTCAAGTTCCAGGGTCTCGAGTTCCGTGCCTAGCCAAAGCGTACACTCGATTGA  4720
 E  R  V  S  A  L  Q  P  G  S  R  D  L  S  S  T  P  L  A  Q  L  I  F  A  V  H
CATGGAGTTCCATCTGTTTCAAGAAACCGACAGCCCTTAAAGGTAGCGTCAACTTTGCCGATGAGCTGTTCAAAATGGAGA  4800
 S  Q  K  D  L  G  R  F  K  F  Q  G  L  E  S  V  P  V  P  S  K  A  Y  T  R  F  D
 M  E  F  H  L  F  Q  E  T  D  S  L  K  G  S  V  N  F  A  D  E  L  F  K  M  E
```

Fig. 1D

```
CTGTTGAAAAATGTCGTCAGAGTATTCTTTGAGATTCTTGAGAAACGGGCTTCAAAGTTCGCGGACACCAGTCTCAATACTT   4880
 L  V  E  N  V  V  R  V  F  F  E  I  L  R  N  G  L  Q  S  S  R  T  P  V  S  I  L
CCTTTGACTGATGGCATTGTGACTCTTGAAAAATTGGATGTTCTCAACGTCAAACATGTCGACTATCCCGAGAATCGAG       4960
 P  L  T  D  G  I  V  T  L  E  K  L  D  V  L  N  V  K  H  V  D  Y  P  R  E  S  S
CTTGGCTGATGTCTTCCAGACCCAAGTCTCTGCTTACCCCGATAGTCTGGCTGTGGTGGACTCCTGTCGCCGATTGACCT      5040
 L  A  D  V  F  Q  T  Q  V  S  A  Y  P  D  S  L  A  V  V  D  S  C  R  L  T
ACACCGAGTTGGATCGCCAGGTCTGCCAGTCGATATTCTCGCTGGATGGCTTCGTCGACGGTCAAATGCCTGCAGAGACGCTTGTCGCA 5120
 Y  T  E  L  D  R  Q  S  D  I  L  A  G  W  L  R  R  R  S  M  P  A  E  T  L  V  A
GTATTGCCCCACGTCAGGTCATGTGAGACAATTGTCGCGTTCTTTGGTGTGTTGAAGGCGAACTTGGCCTATCTTCCTCTGA   5200
 V  F  A  P  R  S  C  E  T  I  V  A  F  F  G  V  L  K  A  N  L  A  Y  L  P  L  D
TGTACGATCGCCCTCGGCGAGAGTTCAGGATATATCGGAGTTTGTTCGTATCCGGATGCGCTGAATGACAGCAATGCAGATGGC  5280
 V  R  S  P  S  A  R  V  Q  D  I  H  L  S  G  L  S  G  P  T  I  V  L  I  G  H  D
CAGGCGCCCTCCCGATATCGAGGTTACTAACGTCGAGTTTGTTCGTATCCGAGCCCTCAGCGCATACGTCCTGTATACCTCAGGATCCACTGG 5360
 T  A  P  P  D  I  E  V  T  N  V  E  F  V  R  I  R  D  A  L  N  D  S  N  A  D  G
TTTGAAGTCATCGAGCACGACACAGACATTGAGCAACCGTGTCATTATTGAACAGTACGAGATCGTACGAGATCTACCAACTATCCTTCGG   5440
 F  E  V  I  E  H  D  S  T  K  P  S  A  T  S  L  A  Y  V  L  Y  T  S  G  S  T  G
CCGACCAAAAGGCGTCATGATTGAGCACGTGTCATTATTGAACAGTACGAGATCGTACGAGATCTACCAACTATCCTTCGG    5520
 R  P  K  G  V  M  I  E  H  R  V  I  I  R  T  V  T  S  G  C  I  P  N  Y  P  S
AAACGAGGATGGCTCACATGGCCACCATTGCGTTTGACGGCGCCATCGAGAGCACTGCAGCTAGACGACTGTGTTTTCGAAGG  5600
 E  T  R  M  A  H  M  A  T  I  A  F  D  G  A  S  Y  E  I  Y  S  A  L  L  F  G  R
ACACTTGTTTGCGTTGACTACATGACAACCCTCGACGCTAGACGCTAGAGACGATGTCAACGC 5680
 T  L  D  A  R  A  L  K  D  V  F  F  R  E  H  V  N  A
GGCAAGTCATGTCACCAGTCTTCTCAAGATGTACCTCTCCGAGTCCCGAGAAGGCTCTCGAGAACCTTGATGTTCTTCT      5760
 A  S  H  V  T  S  S  Q  D  V  P  L  R  V  P  R  R  L  S  R  T  L  M  F  F
TCTTGGTGTGACAGAGATTCGACGGCCCCAGATGCTCTGATGCGCAGGACTTTATCAAGGGGTCCAGTGTTACAATGT       5840
 F  L  V  T  D  S  T  A  P  D  A  L  D  A  Q  G  L  Y  Q  G  V  Q  C  Y  N  G
TACGGCCCAACAGAGAATGGAGTCATGAGTACAATCTATCCCATTGACTGAGTCGTTCATCAATGGAGTCCCAAT          5920
 Y  G  P  T  E  N  G  V  M  S  T  I  Y  P  I  D  S  T  E  S  F  I  N  G  V  P  I
```

Fig. 1E

```
TGGACGAGCTCTGAACAACTCAGGAGCAACAGCTTGTTGTGATGGGAGAGC  6000
 G  R  A  L  N  N  S  G  A  Y  V  V  D  P  E  Q  Q  L  V  G  V  M  G  E
TTGTTGTCACTGGCGATGGTCTTGCGCGGGCTACAGGATGACAAAGCCCGTTTTGTGCACATTACTGTC  6080
 L  V  V  T  G  D  G  L  A  R  G  Y  S  D  K  A  L  D  E  N  R  F  V  H  I  T  V
AATGACCAGAGACAGTGAAGGCCACTCGCGATCGAGTGCGGTACAGGATTGGAGATGGCCTCATCGAGTTCTTCGG  6160
 N  D  Q  T  V  K  A  Y  R  T  G  D  R  V  R  Y  R  I  G  D  G  L  I  E  F  F  G
ACGTATGGACACCCAGTTCAAGATTCGTGGCAATCGTATCGAATCAGCTGAGATTGAAGCGGCCCTTCGCGACTCCT  6240
 R  M  D  T  Q  F  K  I  R  G  N  R  I  E  S  A  E  I  E  A  A  L  R  D  S
CCGTCCGAGATGCTGCTGTCCTTCAGCAGAATGAGGATCAAGCCCTGAGATCTTGGGGTTCTTGTGCTGATCAT  6320
 S  V  R  D  A  A  V  L  Q  Q  N  E  D  Q  A  P  E  I  L  G  F  V  A  D  H
GATCATTCTGAGAATGACAAGGACAATCTGCCAATCAAGTCGAAGGATGGCAAGACCATTCGAGAGTGGCATGTATTC  6400
 D  H  S  E  N  D  K  G  Q  S  A  N  Q  V  E  G  W  Q  D  H  F  E  S  G  M  Y  S
CGACATTGGCGAAATTGACCCCGTTGGTAGCAGCGATTGGAGAGCTTGGTGAGACTACCCGGACACTCAGCAGGTTGGACTCCATGTATGATGGAAGTCAAATCG  6480
 D  I  G  E  I  D  P  S  T  I  G  S  D  F  K  G  W  T  S  M  Y  D  G  S  Q  I
ACTTCGATGAGATGCACGAGTGGCTTGGTGAGACTACCCGGACACTCAGCAGGTTGGACTCCATGTATGATGGAAGTCAAATCG  6560
 D  F  D  E  M  H  E  W  L  G  E  T  T  R  T  L  H  D  N  R  S  L  G  N  V  L  E
ATTGGAACAGGTAGCGGCATGATCCTCTTCAACAAGCTACACCGTAATCCTCTATACCAGTCGCTTGCTGGAAGCCAAGTTCAGGTTGGAACAGCTA  6640
 I  G  T  G  S  G  M  I  L  F  N  L  D  S  R  L  E  S  Y  V  G  L  E  P  S  R  S
AGCAGCTGCATTGTCAACAAAGCTACACACCTGACTTACACCCTGAGTTCTGCTGTGGAAAAGCCAAGTCAGTCATTCAGTATTTCCCGTCTCTTCGGAG  6800
 A  S  S  C  I  V  N  K  A  T  E  S  I  P  S  L  A  G  K  A  K  V  Q  V  G  T  A
CAGATATTGGTCAAGTCCAGAAAATCGCAGACACCTTGATTCATCCGATGTCCAGCGGATTTCTTTGGCAGTCCGATGCCAGC  6880
 T  D  I  G  Q  V  D  D  L  H  P  D  L  V  L  N  S  V  I  Q  Y  F  P  S  S  E
TACCTTGCAGAAATCGCAGACACCTTGATTCATCCGATGTCCAGCGGATTTCTTTGGCAGTCCGATGCCAGC  6880
 Y  L  A  E  I  A  D  T  L  I  H  L  P  N  V  Q  R  I  F  F  G  D  V  R  S  Q  A
CACCAACGAGCACTTCCTGCTGCCAGGCTATCCACACAACTGGGAGAAGACGATGTTGACAGAAAA  6960
 T  N  E  H  F  L  A  A  R  A  I  H  T  L  G  K  N  A  T  K  D  D  V  R  Q  K
TGGCAGAATTGGAGGACATGGAGGAGTTGCTTGTTGAACCTGCTTTCTTCACCTCGTTGAAAGACAGGTTTCCAGGT  7040
 M  A  E  L  E  D  M  E  E  E  L  L  V  E  P  A  F  F  T  S  L  K  D  R  F  P  G
CTGGTGGAACATGTTGAGATCCTGCCAAAGAACATGGAAGTGAATGAGCTCAGTGCCTATCGATATCGCCGCTGTTGT  7120
 L  V  E  H  V  E  I  L  P  K  N  M  E  A  V  N  E  L  S  A  Y  R  Y  A  A  V  V
```

Fig. 1F

```
GCACGTTCGGGGTTCACTTGGAGAGATGAGCTTGTGCTTCCGGTTGAGAAAGATGACTGATGATCGACTTTCAAGCGAATCAAT  7200
 H  V  R  G  S  L  G  D  E  L  V  L  P  V  E  K  D  D  W  I  D  F  Q  A  N  Q
TGAACCAGAAGTCACTGGGTGACCTTCTCAAGTCTTCAGATGCTGTATCATGGCAGTCAGCAAAATTCCTTTCGAAATC        7280
 L  N  Q  K  S  L  G  D  L  L  K  S  S  D  A  I  M  A  V  S  K  I  P  F  E  I
ACGGCCTTTGAAAGACAGGTCGTCGCTTCGCTCCCTCAATAGCAACATCGATGAGTGGCAGCTATCAACCATTCGGTCCAGCGC  7360
 T  A  F  E  R  Q  V  V  A  S  L  N  S  N  I  D  E  W  Q  L  S  T  I  R  S  S  A
CGAGGGCGACTCATCATCCGTTCGCTGTCGAGGTCAGTTCTG                                             7440
 E  G  D  S  S  V  P  D  I  F  R  I  A  G  E  A  G  F  R  V  E  V  S  S
CACGACAGTGGTCTCAGAATGGTGCATTGGACGCTGTGTTTCCATCATTGTTGCTCCCAAGGGCTACTCTGGTCAACTTT      7520
 A  R  Q  W  S  Q  N  G  A  L  D  A  V  F  H  H  C  C  S  Q  G  R  T  L  V  N  F
CCTACGGACCACCATCACCTTCGAGGGTCTGATCTCCTCAGCGACCCTTCAGCGACTGCAAAACCGTCGTATCGCCAT        7600
 P  T  D  H  H  L  R  G  S  D  L  L  T  N  R  P  L  Q  R  L  Q  N  R  R  I  A  I
CGAAGTCCGCGAGAGGCTTCGGTCCTTACTCAGCGAAGGAACTCTCGCAGGGCAAAGTTGTACCGAAGCAGCAGCAGCGCCG   7680
 E  V  R  E  R  L  R  S  L  L  P  S  Y  M  I  P  S  N  I  V  L  D  K  M  P
TCAACGCCAATGGTAAAGTTGACCGAGTGAGTCAGTCAGTCATTCTTTGGAAGAAGCCACTGAGGTGTTTGGCATGAAGGTTGACAT 7840
 L  N  A  N  G  K  V  D  R  K  E  L  S  R  R  A  K  V  P  K  Q  Q  T  A  A  P
TTACCGACATTCCCATCTCTTCAATCTCGGTGACACTCTCTCTTGGCCACGAAGCTCATTTCTCGTATCGACGACTCAAGG    7920
 L  P  T  F  F  P  I  S  E  V  E  V  I  L  C  E  E  A  T  E  V  F  G  M  K  V  D  I
TACCGATCACTTCTTCAAGGATGTCTTTGACCATGGCTTATTGCAGATCTAGCATGGCACCCCGTCAAGGGCTGGGTTG       8000
 T  D  H  F  F  N  L  G  G  H  S  L  L  A  T  K  L  I  S  R  I  D  Q  R  L  K
TCCGTATCACTGTCAAGGATGTCTTTGATGGCTCAGGAGACAAGACAATGGCACCACCCGTACCGAGACTGAAGTATACTCTG   8080
 V  R  I  T  V  K  D  V  F  D  G  S  G  D  K  T  M  A  P  T  E  T  E  A  I  L  C
CAACAACCCGTTTCTGATGGTTCAGGGACAAGACAATTTCTTTGATCTGGTCATTCATCATGG                        8160
 Q  Q  P  V  S  D  G  Q  G  Q  D  R  S  A  H  M  A  P  T  E  T  E  A  I  L  C
TGATGAGTTTGCAAAGGTTCTGGGGTTCCAAGTTGGCATTGGCATCGACTGTTCGTGAAGGATGTTTTCGATCATCCTGTACTC  8240
 D  E  F  A  K  V  L  G  F  Q  V  G  I  T  D  N  F  F  D  L  G  G  H  S  L  M
CTACTAAAACTCGCTGTGCGCCATCGATAACTTGGTTCAATCAAGACCAATAGTTGGAGGTAGAGATGGCTGAATA           8320
 A  T  K  L  A  V  R  I  G  H  R  L  D  T  T  V  S  V  K  D  V  F  D  H  P  V  L
TTCCAACTTGCAATTGCATTGGATAACTTGGTTCAATCAAGACCAATAGTTGGAGGTAGAGATGGCTGAATA
 F  Q  L  A  I  A  L  D  N  L  V  Q  S  K  T  N  E  I  V  G  G  R  E  M  A  E  Y

```
TGCGGGTGAAGTTGAACCAGAGACGGAGCAGGACTGAAGGTTACTGTTATCGCGAAGACGCAGTTATTGGTAGGAAGAGAG  9600
 A  G  E  V  E  P  D  G  A  G  L  K  V  T  V  I  A  K  T  Q  L  F  G  R  K  R
TAGAACATCTGTTGGAGGAAGTTCCAAAACGTTGAGGGTCTCAACTCTTCTTTGTAACGCACGGGTTGGTCTCAATCG    9680
 V  E  H  L  L  E  E  V  S  K  T  F  E  G  L  N  S  L
TCGCGACAGAACAACCGATGTAGTTCGTGTAATTCTTAATGACGTCTTTGACTTTTTTGGTTTTTACCATTCGGAGCAAATA 9760
GTAAGCAGAACACTGCTACGTCGATCGAGTAGTTCAGATATGTCAAAAATTGAGATCTTCAGAACTATTATCTTGTCAGCTTTCA 9840
CATGCTTCGCTACGTCGATCGAGTCGAGTCGATCAAAAATTGAGATCTCAGAACTATTATCTTGACTATTATCTCACGTTGTCAGCTTTCA 9840
CATGCTTCGCTACGTCGATCGAGTCGAGTCGATCAAAAATTGAGATCTCAGAACTACAGGGTAACGCAGAACAATTGACAAGGATTCA 9920
TCGATCGAACACTACTATGATTGGTTCGCGTCTCTGACAGGACCATTTGTCCGTCCAATAATAACAGTAAATAGCTCGCGCTTCTTCGGATTCG 10000
AATGCGACAAGGATTGGAACTATCCGAGTCAGCTTGATCTAGTTGTGTGCGAAGAAGAACGATGACAGCTTGTATTTTGGATATATAAGTTC 10080
CTTTGGTGTATGAATTATCATAGTTTGTGTGCGAAGAAGAACAATAATACCTTGACAATATTGTGTTCCAACATTACACAACACTTGA 10160
ATAAAGGTATGACTCTTCAACATCAAATTAGAAACAATATTGTGTTCCAACATTACACAACACTTGA 10240
ACGGGACACTCYTTCAACATCAAATGATCTGTCCAACAAAGCTGCTACCTTGTCAGTCGCCATCAATCCAT 10320
CGAAGTCAGATCTGCACCTGTTCCAACACCTGGTTGCTTATCAAGACACATGCTGTGCCATGTCGCCATCAATCCAG 10400
TCGACGGAGTGAAGCAGTCCATGGGTAACATGATGTTTGAATGGCTCAAGTATCCTCATCCTTGGCTACGATGTCGCT 10480
GGCGAGGTCATCAAGACGGGACTCGGTGTTAGTCGATTTAAAGAAGGCGATAGAGTTGTGGGTGCTACAGCAGGCATGA 10560
CAAGCGAGGAAGAAGTCCCACCGATGCCAGCCATTTGCAAGAAGTTTGCATCATGCGGCTGCATGCTGCTCAAAAGGATCAA 10640
AGCCGTGTTACGTCCACCGATGCCAGCCAGCCAAGCCATTTGCCTTGTCACGGCTGCATGCTGCTCAAAAGGATCAA 10720
CTGCACTACAACTACCTCAAACCAAGCTCAAAGCGCAGTCAGACAGTCTTGGTTGGGAGCGAGTAACAAG 10800
TGTTGGGAGAAATGCTCCGGCTTGCTGTACAGCTTGCTGTGCGACAGCATCACCTAAGAACTGGGATA 10880
TCGTACGCGGTCTCGCGCTTGTGCAGTTTTTGACTATCACAGTCACGGCCATAAACGTCGACATTGTCTTTTCAAG 10960
GACAAGAAATGCGCAGGTGCGCAGTGCGTAGTGCCTTACCCTCCAATGCGTCACTGAGTCAACAGCCAACAACCAAGATATCCATGATTCCATTG 11040
AGCCACCAACGAAATGTTACCCTCCAATGCGTCACTGAGTCAACAACCAAGATATCCATGATTCCATTG 11120
TCGCAAAGTATTCTGGATGCCGGGAACTGATCGACTCAAGGTTGCGAGCAGTGGAGTGGAGCAGTGGAGTCCAAAGCAAGTTTGTTTTGGT 11200
ACAGACATAATT 11212
```

Fig. 11

# METHODS FOR PRODUCING POLYPEPTIDES IN CYCLOHEXADEPSIPEPTIDE-DEFICIENT CELLS

CROSS-REFERENCE TO RELATED APPLICATION

This application is a continuation-in-part of U.S. application Ser. No. 09/229,862 filed Jan. 13, 1999, now abandoned, which application is fully incorporated herein by reference.

BACKGROUND OF THE INVENTION

1. Field of the Invention

The present invention relates to methods for producing heterologous polypeptides in cyclohexadepsipeptide-deficient filamentous fungal mutant cells. The present invention also relates to mutants of filamentous fungal cells and methods for obtaining the mutant cells. The present invention also relates to isolated cyclohexadepsipeptide synthetases and isolated nucleic acid sequences encoding the cyclohexadepsipeptide synthetases. The present invention also relates to nucleic acid constructs, vectors, and host cells comprising the nucleic acid sequences as well as methods for producing the cyclohexadepsipeptide synthetases. The present invention further relates to cyclohexadepsipeptides produced by the cyclohexadepsipeptide synthetases.

2. Description of the Related Art

Depsipeptides constitute a large class of peptide-related compounds derived from hydroxy and amino acids joined by amide and ester linkages. Many members of this class of compounds are biologically active and include antibiotics, alkaloids, and proteins (Shemyakin et al., 1969, *Journal of Membrane Biology* 1: 402–430). Examples include the enniatins, beauvericin, and bassianolide.

Enniatins are cyclohexadepsipeptide phytoxins with ionophoretic properties produced by various species of actinomycetes and filamentous fungi, particularly strains of *Fusarium*. They are composed of alternating D-2-hydroxyisovaleric acid residues and L-amino acids or N-methyl-L-amino acids to form an 18-membered cyclic structure and may contain more than one species of amino acid.

The biosynthesis of enniatins is catalyzed by enniatin synthetase, which is a large multifunctional enzyme that has all the essential functions for assembling enniatins from their primary precursors, i.e., D-2-hydroxyisovaleric acid, a branched chain L-amino acid (e.g., valine, leucine, isoleucine), S-adenosylmethionine, and ATP (Reper et al., 1995, *European Journal of Biochemistry* 230: 119–126). The precursors (D-2-hydroxyisovaleric acid and branched chain L-amino acid) are activated as thioesters. Covalently bound substrate amino acid residues are methylated under the consumption of S-adenosylmethionine. Then peptide bond formation and cyclization reactions occur.

Enniatins are postulated to play a role in wilt toxic events during infection by enniatin-producing fusaria (Walton, 1990, *Biochemistry of Peptide Antibiotics*, H. Kleinkauf and H. von Dohren, editors, W. de Gruytre, Berlin, pp. 179–203), and also exhibit entomopathogenic properties (Grove and Pople, 1980, *Mycopathologia* 70: 103–105).

The enniatin synthetase gene (esynl) has been cloned from *Fusarium scirpi* (Haese et al., 1993, *Molecular Microbiology* 7: 905–914).

Enniatin synthetase mutants of *Fusarium avenaceum* have been generated that do not produce enniatins (Herrmann et al., 1996, *Molecular Plant-Microbe Interactions* 9: 226–232).

It is an object of the present invention to provide methods for producing heterologous polypeptides in cyclohexadepsipeptide-deficient filamentous fungal mutant cells.

SUMMARY OF THE INVENTION

The present invention relates to methods for producing a heterologous polypeptide, comprising: (a) cultivating a mutant of a parent filamentous fungal cell under conditions conducive for the production of the heterologous polypeptide, wherein (i) the mutant cell comprises a first nucleic acid sequence encoding the heterologous polypeptide, and (ii) the mutant produces less of a cyclohexadepsipeptide than the parent filamentous fungal cell when cultured under the same conditions; and (b) isolating the heterologous polypeptide from the cultivation medium.

The present invention also relates to mutants of filamentous fungal cells and methods for obtaining the mutant cells.

The present invention also relates to isolated cyclohexadepsipeptide synthetases from *Fusarium venenatum* and isolated nucleic acid sequences encoding the cyclohexadepsipeptide synthetases. The invention also relates to nucleic acid constructs, vectors, and host cells comprising the nucleic acid sequences as well as methods for producing the cyclohexadepsipeptide synthetases.

The present invention further relates to cyclohexadepsipeptides produced by the cyclohexadepsipeptide synthetases.

BRIEF DESCRIPTION OF FIGURE

FIG. 1 shows the genomic nucleic acid sequence and the deduced amino acid sequence of a *Fusarium venenatum* ATCC 20334 cyclohexadepsipeptide synthetase (SEQ ID NOS: 1 and 2, respectively).

DETAILED DESCRIPTION OF THE INVENTION

Figure 2:
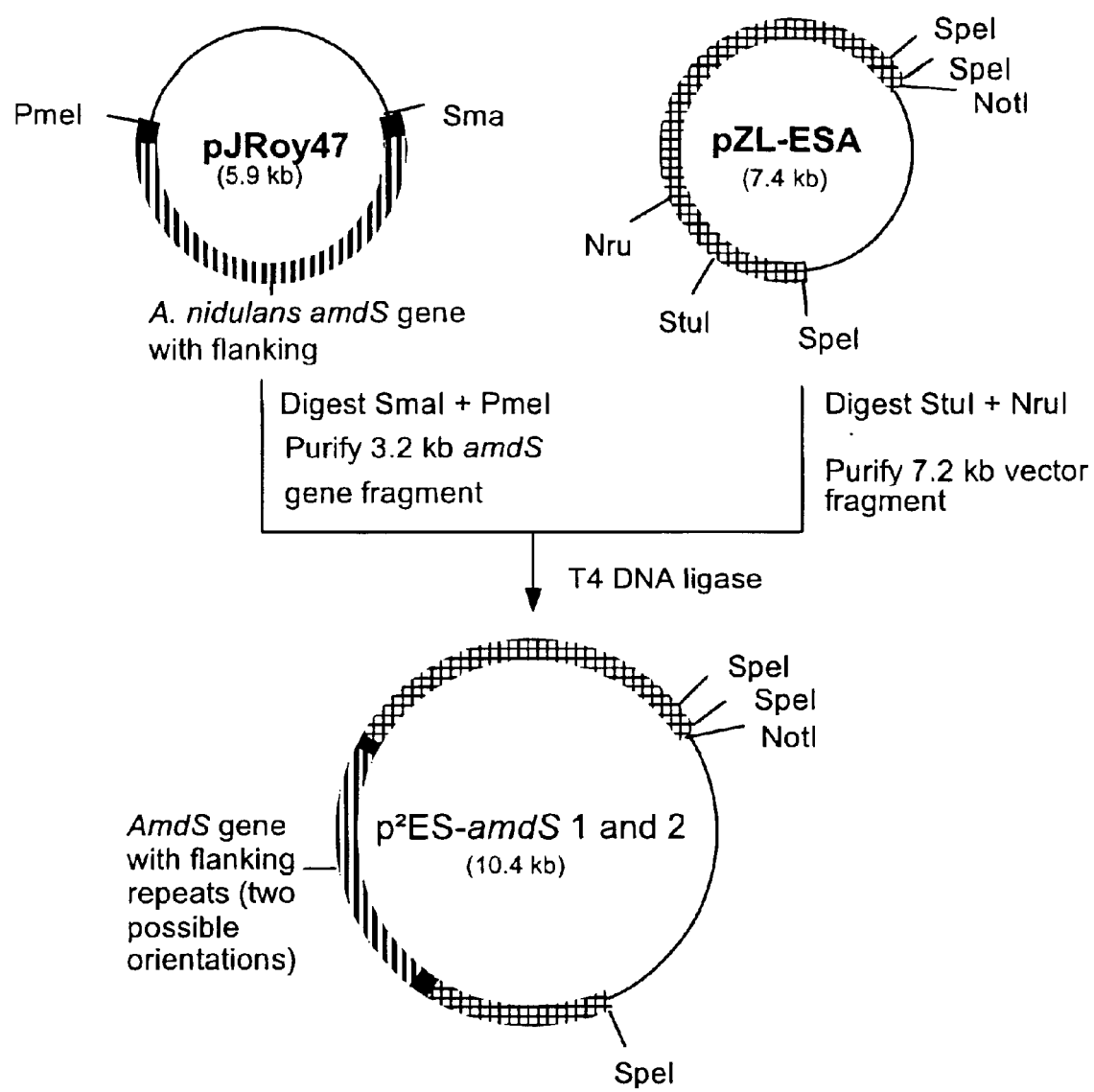
FIG. 2 shows the construction of pΔES-amdS.

The present invention relates to methods for producing a heterologous polypeptide, comprising: (a) cultivating a mutant of a parent filamentous fungal cell under conditions conducive for the production of the heterologous polypeptide, wherein (i) the mutant filamentous fungal cell comprises a first nucleic acid sequence encoding the heterologous polypeptide and (ii) the mutant produces less of a cyclohexadepsipeptide than the parent filamentous fungal cell when cultured under the same conditions; and (b) isolating the heterologous polypeptide from the cultivation medium of the mutant cell.

The term "cyclohexadepsipeptide" is defined herein as a family of peptide-related compounds composed of hydroxy and amino acids linked by amide and ester bonds.

The term "production of a cyclohexadepsipeptide" is defined herein as to include any step involved in the production of a cyclohexadepsipeptide including, but not limited to, biosynthesis, regulation of biosynthesis, transport, and secretion.

In a preferred embodiment, the cyclohexadepsipeptide is an enniatin.

The term "enniatins" is defined herein as a family of cyclohexadepsipeptides composed of three D-2-hydroxyisovaleric acid residues joined alternatively to L-amino acids or N-methyl-L-amino acids to produce an 18-membered cyclic structure. The enniatins include, but are not limited to, enniatin A, A$_1$, B, B$_1$, B$_2$, B$_3$, B$_4$, C, D, E, and F; and derivatives thereof (Visconte et al., 1992, *Journal of Agricultural and Food Chemistry* 40: 1076–1082; Tomodo et al., 1992, *Journal of Antibiotics* 45: 1207–1215), and mixed-type enniatins containing more than one species of amino acid (Zocher et al. 1982, *Biochemistry* 21: 43–48).

In the methods of the present invention, the filamentous fungal cell may be a wild-type cell or a mutant thereof. Furthermore, the filamentous fungal cell may be a cell that does not produce any detectable cyclohexadepsipeptide(s), but contains the genes encoding the cyclohexadepsipeptide (s). Preferably, the filamentous fungal cell is an *Acremonium, Aspergillus, Aureobasidium, Beauveria, Cryptococcus, Filibasidium, Fusarium, Gibberella, Humicola, Magnaporthe, Mucor, Myceliophthora, Myrothecium, Neocallimastix, Neurospora, Paecilomyces, Penicillium, Piromyces, Polyporus, Schizophyllum, Talaromyces, Thermoascus, Thielavia, Tolypocladium,* or *Trichoderma* cell.

In a preferred embodiment, the filamentous fungal cell is an *Aspergillus aculeatus, Aspergillus awamori, Aspergillus foetidus, Aspergillus japonicus, Aspergillus nidulans, Aspergillus niger,* or *Aspergillus oryzae* cell.

In another preferred embodiment, the filamentous fungal cell is a *Fusarium acuminatum, Fusarium avenaceum, Fusarium bactridioides, Fusarium compactum, Fusarium crookwellense* (synonym of *Fusarium cerealis*), *Fusarium culmorum, Fusarium equiseti, Fusarium gibbosum, Fusarium graminearum, Fusarium graminum, Fusarium heterosporum, Fusarium lateritium, Fusarium moniliforme, Fusarium negundi, Fusarium nivale, Fusarium oxysporum, Fusarium reticulatum, Fusarium roseum, Fusarium sambucinum, Fusarium sarcochroum, Fusarium scirpi, Fusarium semitectum, Fusarium solani, Fusarium sporotrichioides, Fusarium sulphureum, Fusarium torulosum, Fusarium trichothecioides, Fusarium tricinctum,* or *Fusarium venenatum* cell.

In another preferred embodiment, the filamentous fungal cell is a *Gibberella pulicaris, Gibberella zeae, Humicola insolens, Humicola lanuginosa, Mucor miehei, Myceliophthora thermophila, Myrothecium roridin, Neurospora crassa, Paeciliomyces fumoso-roseus, Penicillium purpurogenum,* or *Polyporus sulphureus* cell.

In another preferred embodiment, the filamentous fungal cell is a *Trichoderma harzianum, Trichoderma koningii, Trichoderma longibrachiatum, Trichoderma reesei,* or *Trichoderma viride* cell.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another more preferred embodiment, the *Fusarium venenatum* cell is a morphological mutant of *Fusarium venenatum* A3/5 or *Fusarium venenatum* ATCC 20334, as disclosed in WO 97/26330.

The filamentous fungal cell may also be a cell involved in the production of products containing (parts of) the mycelium, for example, in the production of the product QUORN™ (Marlow Foods, Ltd., Great Britain), which is produced from a *Fusarium* strain.

In the methods of the present invention, the mutant cell comprises a second nucleic acid sequence which comprises a modification of at least one of the genes involved in the production of the cyclohexadepsipeptide. Any gene of a filamentous fungal cell involved in the production of a cyclohexadepsipeptide may be modified. In a preferred embodiment, the gene is a cylcohexadepsipeptide synthetase gene. In a more preferred embodiment, the gene is an enniatin synthetase gene. In another more preferred embodiment, the gene is a D-hydroxyisovalerate dehydrogenase gene. D-Hydroxyisovalerate dehydrogenase catalyzes the conversion of 2-ketoisovalerate to D-hydroxyisovalerate (Lee and Zocher, 1996, *Journal of Biochemistry and Molecular Biology* 29: 493–499). In an even more preferred embodiment, the gene is a *Fusarium venenatum* cyclohexadepsipeptide synthetase gene having (a) a nucleic acid sequence encoding a polypeptide having an amino acid sequence which has at least 65% identity with the mature polypeptide contained within SEQ ID NO:2; (b) a nucleic acid sequence having at least 65% homology with the mature polypeptide coding region of SEQ ID NO:1; (c) a nucleic acid sequence which hybridizes under medium stringency conditions with (i) the nucleic acid sequence of SEQ ID NO:1, (ii) the cDNA sequence of SEQ ID NO:1, (iii) a subsequence of (i) or (ii) of at least 100 nucleotides, or (iv) a complementary strand of (i), (ii), or (iii); (d) an allelic variant of (a), (b), or (c); or (e) a subsequence of (a), (b), (c), or (d), wherein the subsequence encodes a polypeptide fragment which has cyclohexadepsipeptide synthetase activity. In a most preferred embodiment, the gene is a *Fusarium venenatum* cyclohexadepsipeptide synthetase gene having the nucleic acid sequence of SEQ ID NO:1.

The cyclohexadepsipeptide-deficient filamentous fungal mutant cell may be constructed by reducing or eliminating expression of one or more of the genes described above using methods well known in the art, for example, insertions, disruptions, replacements, or deletions. The gene to be modified or inactivated may be, for example, the coding region or a part thereof essential for activity, or a regulatory element of the gene required for the expression of the coding region. An example of such a regulatory or control sequence may be a promoter sequence or a functional part thereof, i.e., a part that is sufficient for affecting expression of the nucleic acid sequence. Other control sequences for possible modification include, but are not limited to, a leader, polyadenylation sequence, propeptide sequence, signal peptide sequence, transcription terminator, and transcriptional activator.

Modification or inactivation of the gene may be performed by subjecting the parent cell to mutagenesis and selecting for mutant cells in which expression of the gene has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the gene may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the gene to be modified, it is preferred that the modification be performed in vitro as exemplified below.

An example of a convenient way to eliminate or reduce production of a cyclohexadepsipeptide by a filamentous fungal cell of choice is based on techniques of gene replacement, gene deletion, or gene disruption. For example, in the gene disruption method, a nucleic acid sequence corresponding to the endogenous gene or gene fragment of interest is mutagenized in vitro to produce a defective nucleic acid sequence which is then transformed into the parent cell to produce a defective gene. By homologous recombination, the defective nucleic acid sequence replaces the endogenous gene or gene fragment. It may be desirable that the defective gene or gene fragment also encodes a marker that may be used for selection of transformants in which the nucleic acid sequence has been modified or destroyed. In a particularly preferred embodiment, the gene is disrupted with a selectable marker such as those described herein.

Alternatively, modification or inactivation of the gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

A nucleic acid sequence complementary or homologous to the nucleic acid sequence of a gene involved in the production of a cyclohexadepsipeptide may be obtained from other microbial sources that produce cyclohexadepsipeptides.

Preferred sources for an enniatin synthetase gene having a nucleic acid sequence complementary or homologous to the nucleic acid sequence of SEQ ID NO:1 of *Fusarium venenatum* include other *Fusarium* strains. A more preferred source is *Fusarium scirpi* (Haese et al., 1993, supra).

Preferred sources for D-hydroxyisovalerate dehydrogenase genes that may be complementary or homologous to the nucleic acid sequence of the corresponding genes of a filamentous fungal cell include other *Fusarium* strains. A more preferred source for the D-hydroxyisovalerate dehydrogenase gene is *Fusarium sambucinum* (Lee and Zocher, 1996, supra). Furthermore, the nucleic acid sequences may be native to the filamentous fungal cell.

The level of cyclohexadepsipeptides produced by a mutant filamentous fungal cell of the present invention may be determined using the method of Visconti et al., 1992, *Journal of Agriculture and Food Chemistry* 40: 1076–1082. Specifically, one ml of *Fusarium venenatum* cell-free culture broth is extracted twice with 2.0 ml ethyl acetate. The combined organic extracts are evaporated to dryness under a stream of nitrogen gas and redissolved in 0.5 ml hexane. One microliter samples are analyzed using a Hewlett-Packard 6890 GC/Series MSD system operating in the electron impact (EI) mode. Samples are injected on-column and separated utilizing a DB-5 capillary column (30 m×0.25 mm, 0.25 μm film) employing a temperature program with heating from 120 to 300° C. at a rate of 15° C./min. For example, enniatins A, A1, B, B1, B2 and B3 are identified by m/z ratios for the ($M^+$+H) ion of 682, 668, 640, 654, 626 and 612, respectively.

The mutant filamentous fungal cell preferably produces at least about 25% less, more preferably at least about 50% less, even more preferably at least about 75% less, most preferably at least about 95% less, and even most preferably no cyclohexadepsipeptide than the corresponding parent filamentous fungal cell when cultured under identical conditions. The parent and mutant cells may be compared with regard to production of a cyclohexadepsipeptide under conditions conducive for the production of a polypeptide of interest or under conditions conducive for the production of a cyclohexadepsipeptide.

In another aspect of the present invention, the mutant filamentous fungal cell may additionally contain modifications of one or more third nucleic acid sequences that encode proteins that may be detrimental to the production, recovery, and/or application of the heterologous polypeptide of interest. The modification reduces or eliminates expression of the one or more third nucleic acid sequences resulting in a mutant cell that may produce more of the heterologous polypeptide than the mutant cell without the modification of the third nucleic acid sequence when cultured under the same conditions. The third nucleic acid sequence may encode any protein or enzyme. For example, the enzyme may be an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase. The third nucleic acid sequence preferably encodes a proteolytic enzyme, e.g., an aminopeptidase, carboxypeptidase, or endoprotease.

The mutant filamentous fungal cell is cultivated in a nutrient medium suitable for production of a heterologous polypeptide of interest using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the heterologous polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted heterologous polypeptide can be recovered directly from the medium.

The heterologous polypeptide may be detected using methods known in the art that are specific for the polypeptide. These detection methods may include use of specific antibodies, formation of an enzyme product, disappearance of an enzyme substrate, or SDS-PAGE. For example, an enzyme assay may be used to determine the activity of the heterologous polypeptide. Procedures for determining enzyme activity are known in the art for many enzymes.

The resulting heterologous polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J.-C. Janson and Lars Ryden, editors, VCH Publishers, New York, 1989).

The polypeptide may be any polypeptide heterologous to the mutant filamentous fungal cell. The term "polypeptide" is not meant herein to refer to a specific length of the encoded product and, therefore, encompasses peptides, oligopeptides, and proteins. The term "heterologous polypeptide" is defined herein as a polypeptide that is not native to the fungal cell, a native protein in which modifications have been made to alter the native sequence, or a native protein whose expression is quantitatively altered as a result of a manipulation of the fungal cell by recombinant DNA techniques. The mutant fungal cell may contain one or more copies of the nucleic acid sequence encoding the polypeptide. In a preferred embodiment, the heterologous polypeptide is an extracellularly secreted polypeptide.

Preferably, the heterologous polypeptide is a hormone, hormone variant, enzyme, receptor or portion thereof, antibody or portion thereof, or reporter. In a more preferred embodiment, the heterologous polypeptide is an oxidoreductase, transferase, hydrolase, lyase, isomerase, or ligase. In an even more preferred embodiment, the heterologous polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase or xylanase.

The nucleic acid sequence encoding a heterologous polypeptide that can be expressed in a filamentous fungal cell may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

In the methods of the present invention, the mutant filamentous fungal cell may also be used for the recombinant production of polypeptides that are native to the cell. The native polypeptides may be recombinantly produced by, e.g., placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the cell. The present invention also encompasses, within the scope of the term "heterologous polypeptide", such recombinant production of homologous polypeptides, to the extent that such expression involves the use of genetic elements not native to the cell, or use of native elements that have been manipulated to function in a manner that do not normally occur in the host cell.

The techniques used to isolate or clone a nucleic acid sequence encoding a heterologous polypeptide are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

In the methods of the present invention, heterologous polypeptides may also include fused or hybrid polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the mutant filamentous fungal cell.

An isolated nucleic acid sequence encoding a heterologous polypeptide of interest may be manipulated in a variety of ways to provide for expression of the polypeptide. Expression will be understood to include any step involved in the production of the polypeptide including, but not limited to, transcription, post-transcriptional modification, translation, post-translational modification, and secretion. Manipulation of the nucleic acid sequence prior to its insertion into a vector may be desirable or necessary depending on the expression vector. The techniques for modifying nucleic acid sequences utilizing cloning methods are well known in the art.

"Nucleic acid construct" is defined herein as a nucleic acid molecule, either single- or double-stranded, isolated from a naturally occurring gene or modified to contain segments of nucleic acid that are combined and juxtaposed in a manner which would not otherwise exist in nature. The term nucleic acid construct is synonymous with the term expression cassette when the nucleic acid construct contains all the control sequences required for expression of a coding sequence. The term "coding sequence" as defined herein is a sequence that is transcribed into mRNA and translated into a polypeptide. The boundaries of the coding sequence are generally determined by the ATG start codon located just upstream of the open reading frame at the 5' end of the mRNA and a transcription terminator sequence located just downstream of the open reading frame at the 3' end of the mRNA. A coding sequence can include, but is not limited to, genomic, cDNA, RNA, semisynthetic, synthetic, recombinant, or any combinations thereof.

The term "control sequences" is defined herein to include all components that are necessary or advantageous for the expression of a heterologous polypeptide. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a heterologous polypeptide. The term "operably linked" is defined herein as a configuration in which a control sequence is appropriately placed at a position relative to the coding sequence of the DNA sequence such that the control sequence directs the production of a heterologous polypeptide.

The control sequence may be an appropriate promoter sequence, a nucleic acid sequence that is recognized by a filamentous fungal cell for expression of the nucleic acid sequence. The promoter sequence contains transcriptional control sequences that mediate the expression of the heterologous polypeptide. The promoter may be any nucleic acid sequence that shows transcriptional activity in the filamentous fungal cell including mutant, truncated, and hybrid promoters, and may be obtained from genes encoding extracellular or intracellular polypeptides either homologous or heterologous to the cell.

Examples of suitable promoters for directing the transcription of the nucleic acid constructs in the methods of the present invention are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Aspergillus oryzae* acetamidase (amdS), *Fusarium oxysporum* trypsin-like protease (U.S. Pat. No. 4,288,627), and mutant, truncated, and hybrid promoters thereof. Particularly preferred promoters are the NA2-tpi (a hybrid of the promoters from the genes encoding *Aspergillus niger* neutral alpha-amylase and *Aspergillus oryzae* triose phosphate isomerase), glucoamylase, and TAKA amylase promoters.

The control sequence may also be a suitable transcription terminator sequence, a sequence recognized by a filamentous fungal cell to terminate transcription. The terminator sequence is operably linked to the 3' terminus of the nucleic acid sequence encoding the heterologous polypeptide. Any terminator that is functional in the filamentous fungal cell may be used in the present invention.

Preferred terminators are obtained from the genes encoding *Aspergillus oryzae* TAKA amylase, *Aspergillus niger* glucoamylase, *Aspergillus nidulans* anthranilate synthetase, *Aspergillus niger* alpha-glucosidase, and *Fusarium oxysporum* trypsin-like protease.

The control sequence may also be a suitable leader sequence, a nontranslated region of a mRNA that is important for translation by the filamentous fungal cell. The leader sequence is operably linked to the 5' terminus of the nucleic acid sequence encoding the heterologous polypeptide. Any leader sequence that is functional in the filamentous fungal cell may be used in the present invention.

Preferred leaders are obtained from the genes encoding *Aspergillus oryzae* TAKA amylase and *Aspergillus nidulans* triose phosphate isomerase.

The control sequence may also be a polyadenylation sequence, a sequence operably linked to the 3' terminus of the nucleic acid sequence and, when transcribed, is recognized by a filamentous fungal cell as a signal to add polyadenosine residues to transcribed mRNA. Any polyadenylation sequence that is functional in the filamentous fungal cell may be used in the present invention.

Preferred polyadenylation sequences are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The control sequence may also be a signal peptide coding region that codes for an amino acid sequence linked to the amino terminus of the heterologous polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. The signal peptide coding region may be obtained from a glucoamylase or an amylase gene from an *Aspergillus* species, or a lipase or proteinase gene from a *Rhizomucor* species. However, any signal peptide coding region that directs the expressed heterologous polypeptide into the secretory pathway of a filamentous fungal cell may be used in the present invention.

An effective signal peptide coding region is the signal peptide coding region obtained from the genes encoding *Aspergillus oryzae* TAKA amylase, *Aspergillus niger* neutral amylase, *Rhizomucor miehei* aspartic proteinase gene, and *Humicola lanuginosa* cellulase.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from the genes encoding *Rhizomucor miehei* aspartic proteinase and *Myceliophthora thermophila* laccase (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

The nucleic acid constructs may also comprise one or more nucleic acid sequences that encode one or more factors that are advantageous for directing the expression of the heterologous polypeptide, e.g., a transcriptional activator (e.g., a trans-acting factor), chaperone, and processing protease. Any factor that is functional in a filamentous fungal cell may be used in the present invention. The nucleic acids encoding one or more of these factors are not necessarily in tandem with the nucleic acid sequence encoding the heterologous polypeptide.

It may also be desirable to add regulatory sequences that allow the regulation of the expression of the heterologous polypeptide relative to the growth of the filamentous fungal cell. Examples of regulatory systems are those that cause the expression of the gene to be turned on or off in response to a chemical or physical stimulus, including the presence of a regulatory compound. The TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification, e.g., the metallothionein genes which are amplified with heavy metals. In these cases, the nucleic acid sequence encoding the heterologous polypeptide would be operably linked with the regulatory sequence.

The various nucleic acid and control sequences described above may be joined together to produce a recombinant expression vector that may include one or more convenient restriction sites to allow for insertion or substitution of the nucleic acid sequence encoding the heterologous polypeptide at such sites. Alternatively, the nucleic acid sequence encoding the heterologous polypeptide may be expressed by inserting the sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) that can be conveniently subjected to recombinant DNA procedures and can bring about the expression of the nucleic acid sequence encoding the heterologous polypeptide. The choice of the vector will typically depend on the compatibility of the vector with the filamentous fungal cell into which the vector is to be introduced. The vector may be a linear or closed circular plasmid. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the filamentous fungal cell, is integrated into the genome and replicated together with the chromosome(s) into which it has been integrated. The vector system may be a single vector or plasmid or two or more vectors or plasmids that together contain the total DNA to be introduced into the genome of the filamentous fungal cell, or a transposon.

The vector preferably contains one or more selectable markers that permit easy selection of transformed filamentous fungal cells. A selectable marker is a gene the product of which provides for biocide or viral resistance, resistance to heavy metals, prototrophy to auxotrophs, and the like. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in a filamentous fungal cell are the amdS and pyrG genes of *Aspergillus nidulans* or *Aspergillus oryzae* and the bar gene of *Streptomyces hygroscopicus*.

The vector preferably contains an element(s) that permits stable integration of the vector into a filamentous fungal cell genome or autonomous replication of the vector in the cell independent of the genome of the cell.

"Introduction" means introducing a vector comprising the nucleic acid sequence into a filamentous fungal cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the chromosome occurs by homologous recombination, non-homologous recombination, or transposition.

The introduction of an expression vector into a filamentous fungal cell may involve a process consisting of protoplast formation, transformation of the protoplasts, and regeneration of the cell wall in a manner known per se. Suitable procedures for transformation of *Aspergillus* host cells are described in EP 23 8 023 and Yelton et al., 1984, *Proceedings of the National Academy of Sciences USA* 81: 1470–1474. A suitable method of transforming *Fusarium* species is described by Malardier et al., 1989, *Gene* 78: 147–156 or in WO 96/00787.

For integration into the genome of a filamentous fungal cell, the vector may rely on the nucleic acid sequence encoding the heterologous polypeptide or any other element of the vector for stable integration of the vector into the genome by homologous or nonhomologous recombination. Alternatively, the vector may contain additional nucleic acid sequences for directing integration by homologous recombination into the genome of the filamentous fungal cell. The additional nucleic acid sequences enable the vector to be integrated into the genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequences that are homologous with the target sequence in the genome of the filamentous fungal cell. Furthermore, the integrational elements may be non-encoding or encoding nucleic acid sequences. On the other hand, the vector may be integrated into the genome of the cell by non-homologous recombination.

For autonomous replication, the vector may further comprise an origin of replication enabling the vector to replicate autonomously in the filamentous fungal cell in question.

It will be understood that the methods of the present invention are not limited to a particular order for obtaining the mutant filamentous fungal cell. The modification of a gene involved in the production of a cyclohexadepsipeptide may be introduced into the parent cell at any step in the construction of the cell for the production of a heterologous polypeptide. It is preferable that the filamentous fungal mutant has already been made cyclohexadepsipeptide-deficient using the methods of the present invention prior to the introduction of a gene encoding a heterologous polypeptide.

The procedures used to ligate the elements described herein to construct the recombinant expression vectors are well known to one skilled in the art (see, e.g., J. Sambrook, E. F. Fritsch, and T. Maniatus, 1989, *Molecular Cloning, A Laboratory Manual,* 2d edition, Cold Spring Harbor, N.Y.).

The present invention also relates to methods for obtaining cyclohexadepsipeptide-deficient filamentous fungal mutant cells which comprise (a) introducing into a parent filamentous fungal cell a first nucleic acid sequence comprising a modification of at least one of the genes involved in the production of a cyclohexadepsipeptide and a second nucleic acid sequence encoding a heterologous polypeptide; and (b) identifying the mutant from step (a) comprising the modified nucleic acid sequence, wherein the mutant cell produces less of the cyclohexadepsipeptide than the parent filamentous fungal cell of the mutant cell when cultured under the same conditions.

The present invention also relates to cyclohexadepsipeptide-deficient mutants of filamentous fungal cells for producing a heterologous polypeptide which comprise a first nucleic acid sequence comprising a modification of at least one of the genes involved in the production of a cyclohexadepsipeptide and a second nucleic acid sequence encoding the heterologous polypeptide, wherein the mutant produces less of the cyclohexadepsipeptide than the parent filamentous fungal cell of the mutant cell when cultured under the same conditions.

The present invention also relates to isolated cyclohexadepsipeptide synthetases. The term "cyclohexadepsipeptide synthetase activity" is defined herein as a synthetase activity which catalyzes the production of a cyclohexadepsipeptide from D-2-hydroxyisovaleric acid, a branched chain L-amino acid (e.g., valine, leucine, isoleucine), S-adenosylmethionine, and ATP. For purposes of the present invention, cyclohexadepsipeptide synthetase activity is determined by measuring the production of a cyclohexadepsipeptide according to the procedure of Zocher et al., 1982, *Biochemistry* 21: 43–48. Specifically, the cyclohexadepsipeptide synthetase is incubated with 1 mM valine, 0.2 mM S-adenosylmethionine, 0.2 mM D-2-hydroxyisovaleric acid, 4 mM ATP, and 4 mM Mg(OAc)$_2$ in a total volume of 100 $\mu$l for 10 minutes at 37° C. in 50 mM MOPS pH 7.0. The amount of cyclohexadepsipeptide is determined as described herein based on the method of Visconti et al., 1992, supra. One unit of cyclohexadepsipeptide synthetase activity is defined as 1.0 $\mu$mole of cyclohexadepsipeptide produced per minute at 37° C., pH 7.0.

In a first embodiment, the present invention relates to isolated cyclohexadepsipeptide synthetases having an amino acid sequence which has a degree of identity to the mature polypeptide contained within SEQ ID NO:2 of at least about 65%, preferably at least about 70%, more preferably at least about 80%, even more preferably at least about 90%, most preferably at least about 95%, and even most preferably at least about 97%, which have cyclohexadepsipeptide synthetase activity hereinafter "homologous cyclohexadepsipeptide synthetases"). In a preferred embodiment, the homologous cyclohexadepsipeptide synthetases have an amino acid sequence which differs by five amino acids, preferably by four amino acids, more preferably by three amino acids, even more preferably by two amino acids, and most preferably by one amino acid from the mature polypeptide contained within SEQ ID NO:2. For purposes of the present invention, the degree of identity between two amino acid sequences is determined by the Clustal method (Higgins, 1989, CABIOS 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Preferably, the cyclohexadepsipeptide synthetases of the present invention comprise the amino acid sequence of SEQ ID NO:2 or an allelic variant thereof; or a fragment thereof that has cyclohexadepsipeptide synthetase activity. In a more preferred embodiment, the cyclohexadepsipeptide synthetase of the present invention comprises the amino acid sequence of SEQ ID NO:2. In another preferred embodiment, the cyclohexadepsipeptide synthetase of the present invention comprises the mature polypeptide contained within SEQ ID NO:2, or an allelic variant thereof; or a fragment thereof that has cyclohexadepsipeptide synthetase activity. In another preferred embodiment, the cyclohexadepsipeptide synthetase of the present invention comprises the mature polypeptide contained within SEQ ID NO:2. In another preferred embodiment, the cyclohexadepsipeptide synthetase of the present invention consists of the amino acid sequence of SEQ ID NO:2 or an allelic variant thereof; or a fragment thereof that has cyclohexadepsipeptide synthetase activity. In another preferred embodiment, the cyclohexadepsipeptide synthetase of the present invention consists of the amino acid sequence of SEQ ID NO:2. In another preferred embodiment, the cyclohexadepsipeptide synthetase consists of the mature polypeptide contained within SEQ ID NO:2 or an allelic variant thereof; or a fragment thereof that has cyclohexadepsipeptide synthetase activity. In another preferred embodiment, the cyclohexadepsipeptide synthetase consists of the mature polypeptide contained within SEQ ID NO:2.

A fragment of SEQ ID NO:2 is a polypeptide having one or more amino acids deleted from the amino and/or carboxyl terminus of this amino acid sequence. Preferably, a fragment contains at least 2854 amino acid residues, more preferably at least 2954 amino acid residues, and most preferably at least 3054 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous cyclohexadepsipeptide synthetases may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated cyclohexadepsipeptide synthetases encoded by nucleic acid sequences that hybridize under low stringency conditions, more preferably medium stringency conditions, even more preferably high stringency conditions, and most preferably very high stringency conditions with a nucleic acid probe that hybridizes under the same conditions with (i) the nucleic acid sequence of SEQ ID NO:1, (ii) the cDNA sequence of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1 may be at least 100 nucleotides or preferably at least 200 nucleotides. Moreover, the subsequence may encode a polypeptide fragment that has cyclohexadepsipeptide synthetase activity. The cyclohexadepsipeptide synthetases may also be allelic variants or fragments that have cyclohexadepsipeptide synthetase activity. The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding cyclohexadepsipeptide synthetases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA that hybridizes with the probes described above and encodes a cyclohexadepsipeptide synthetase. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:1 or a subsequence thereof, the carrier material is used in a Southern blot. For purposes of the present invention, hybridization indicates that the nucleic acid sequence hybridizes to a nucleic acid probe corresponding to (i) the nucleic acid sequence of SEQ ID NO:1, (ii) the cDNA sequence of SEQ ID NO:1, (iii) a subsequence of (i) or (ii), or (iv) a complementary strand of (i), (ii), or (iii) under low to very high stringency conditions. Molecules to which the nucleic acid probe hybridizes under these conditions are detected using X-ray film.

In a preferred embodiment, the nucleic acid probe is a nucleic acid sequence that encodes the cyclohexadepsipeptide synthetase of SEQ ID NO:2, or a subsequence thereof. In another preferred embodiment, the nucleic acid probe is SEQ ID NO:1. In another preferred embodiment, the nucleic acid probe is the mature polypeptide coding region contained within SEQ ID NO:1. In another preferred embodiment, the nucleic acid probe is the nucleic acid sequences contained in plasmid pZL-ESA, which is contained in *Escherichia coli* NRRL B-30068, plasmid pZL-ESB, which is contained in *Escherichia coli* NRRL B-30069, and plasmid pZL-ESC, which is contained in *Escherichia coli* NRRL B-30070, wherein the nucleic acid sequences encode the cyclohexadepsipeptide synthetase of SEQ ID NO:2. In another preferred embodiment, the nucleic acid probe is the nucleic acid sequence encoding the mature cyclohexadepsipeptide synthetase of SEQ ID NO:2 contained in plasmid pZL-ESA, which is contained in *Escherichia coli* NRRL B-30068, plasmid pZL-ESB, which is contained in *Escherichia coli* NRRL B-30069, and plasmid pZL-ESC, which is contained in *Escherichia coli* NRRL B-30070.

For long probes of at least 100 nucleotides in length, low to very high stringency conditions are defined as prehybridization and hybridization at 45° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes that are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to isolated polypeptides having immunochemical identity or partial immunochemical identity to the cyclohexadepsipeptide synthetase having the amino acid sequence of SEQ ID NO:2 or the mature polypeptide thereof. The immunochemical properties are determined by immunological cross-reaction identity tests by the well-known Ouchterlony double immunodiffusion procedure. Specifically, an antiserum containing polyclonal antibodies that are immunoreactive or bind to epitopes of the polypeptide having the amino acid sequence of SEQ ID NO:2 or the mature polypeptide thereof are prepared by immunizing rabbits (or other rodents) according to the procedure described by Harboe and Ingild, In N. H. Axelsen, J. Krøll, and B. Weeks, editors, A Manual of Quantitative Immunoelectrophoresis, Blackwell Scientific Publications, 1973, Chapter 23, or Johnstone and Thorpe, Immunochemistry in Practice, Blackwell Scientific Publications, 1982 (more specifically pages 27–31). A polypeptide having immunochemical identity is a polypeptide that reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, A Manual of Quantitative Immunoelectrophoresis, Blackwell Scientific Publications, 1973, Chapter 10. A polypeptide having partial immunochemical identity is a polypeptide that reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, A Manual of Quantitative Immunoelectrophoresis, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, Antibodies, A Laboratory Manual, Cold Spring Harbor Press, Cold Spring Harbor, N.Y. .

The isolated cyclohexadepsipeptide synthetases of the present invention have at least 20%, preferably at least 40%, more preferably at least 60%, even more preferably at least 80%, even more preferably at least 90%, and most preferably at least 100% of the cyclohexadepsipeptide synthetase activity of the mature polypeptide of SEQ ID NO:2.

In a preferred embodiment, a cyclohexadepsipeptide synthetase of the present invention is obtained from a *Fusarium venenatum* strain, and more preferably from *Fusarium venenatum* ATCC 20334 or a mutant strain thereof, e.g., the polypeptide with the amino acid sequence of SEQ ID NO:2.

As defined herein, an "isolated" cyclohexadepsipeptide synthetase is a polypeptide that is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

A cyclohexadepsipeptide synthetase of the present invention may be obtained from microorganisms of any genus.

A cyclohexadepsipeptide synthetase of the present invention may be a bacterial cyclohexadepsipeptide synthetase. For example, the cyclohexadepsipeptide synthetase may be a gram positive bacterial cyclohexadepsipeptide synthetase such as a *Bacillus* cyclohexadepsipeptide synthetase, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* cyclohexadepsipeptide synthetase; or a *Streptomyces* cyclohexadepsipeptide synthetase, e.g., a *Streptomyces lividans* or *Streptomyces murinus* cyclohexadepsipeptide synthetase; or a gram negative bacterial cyclohexadepsipeptide synthetase, e.g., an *E. coli* or a *Pseudomonas* sp. cyclohexadepsipeptide synthetase.

A cyclohexadepsipeptide synthetase of the present invention may be a fungal cyclohexadepsipeptide synthetase, and more preferably a yeast cyclohexadepsipeptide synthetase such as a *Candida, Kluyveromyces, Pichia, Saccharomyces, Schizosaccharomyces*, or *Yarrowia* cyclohexadepsipeptide synthetase; or more preferably a filamentous fungal cyclohexadepsipeptide synthetase such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* cyclohexadepsipeptide synthetase.

In a preferred embodiment, the cyclohexadepsipeptide synthetase is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cyclohexadepsipeptide synthetase.

In another preferred embodiment, the cyclohexadepsipeptide synthetase is an *Aspergillus aculeatus, Aspergillus awamori, Aspergillus foetidus, Aspergillus japonicus, Aspergillus nidulans, Aspergillus niger, Aspergillus oryzae, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* cyclohexadepsipeptide synthetase.

In another preferred embodiment, the cyclohexadepsipeptide synthetase is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cyclohexadepsipeptide synthetase.

The present invention also relates to isolated nucleic acid sequences that encode a cyclohexadepsipeptide synthetase of the present invention. In a preferred embodiment, the nucleic acid sequence is set forth in SEQ ID NO:1. In another more preferred embodiment, the nucleic acid sequence is the sequences contained in plasmid pZL-ESA, which is contained in *Escherichia coli* NRRL B-30068, plasmid pZL-ESB, which is contained in *Escherichia coli* NRRL B-30069, and plasmid pZL-ESC, which is contained in *Escherichia coli* NRRL B-30070. In another more preferred embodiment, the nucleic acid sequence is the sequences encoding the mature polypeptide contained within SEQ ID NO:2 that is contained in plasmid pZL-ESA, which is contained in *Escherichia coli* NRRL B-30068, plasmid pZL-ESB, which is contained in *Escherichia coli* NRRL B-30069, and plasmid pZL-ESC, which is contained in *Escherichia coli* NRRL B-30070. In another preferred embodiment, the nucleic acid sequence is the mature polypeptide coding region contained within SEQ ID NO:1. The present invention also encompasses nucleic acid sequences that encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 that encode fragments of SEQ ID NO:2, which have cyclohexadepsipeptide synthetase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 8562 nucleotides, more preferably at least 8862 nucleotides, and most preferably at least 9162 nucleotides.

The present invention also relates to mutant nucleic acid sequences comprising at least one mutation in the mature polypeptide coding sequence of SEQ ID NO:1, in which the mutant nucleic acid sequence encodes a polypeptide which consists of the mature polypeptide contained within SEQ ID NO:2.

The techniques used to isolate or clone a nucleic acid sequence encoding a cyclohexadepsipeptide synthetase may include isolation from genomic DNA, preparation from cDNA, or a combination thereof, as described herein. The cloning of the nucleic acid sequences of the present invention from such genomic DNA can be effected, e.g., by PCR or other nucleic acid amplification procedures such as ligase chain reaction (LCR), ligated activated transcription (LAT) and nucleic acid sequence-based amplification (NASBA) may be used. The nucleic acid sequence may be cloned from a strain of *Fusarium*, or another or related organism and thus, for example, may be an allelic or species variant of the polypeptide encoding region of the nucleic acid sequence. The nucleic acid sequence may be of genomic, cDNA, RNA, semisynthetic, synthetic origin, or any combinations thereof.

The term "isolated nucleic acid sequence" as used herein refers to a nucleic acid sequence that is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis.

The present invention also relates to nucleic acid sequences that have a degree of homology to the mature polypeptide coding region contained within SEQ ID NO:1 of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=3, gap penalty=3, and windows=20.

Modification of a nucleic acid sequence encoding a cyclohexadepsipeptide synthetase of the present invention may be necessary for the synthesis of polypeptides substantially similar to the cyclohexadepsipeptide synthetase. The term "substantially similar" to the cyclohexadepsipeptide synthetase refers to non-naturally occurring forms of the enzyme. These polypeptides may differ in some engineered way from the cyclohexadepsipeptide synthetase isolated from its native source, e.g., variants of the cyclohexadepsipeptide synthetase that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions that do not give rise to another amino acid sequence of the polypeptide encoded by the nucleic acid sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the cyclohexadepsipeptide synthetase encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for cyclohexadepsipeptide synthetase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a cyclohexadepsipeptide synthetase of the present invention, which hybridize under low stringency conditions, more preferably medium stringency conditions, even more preferably high stringency conditions, and most preferably very high stringency conditions as defined herein with a nucleic acid probe that hybridizes under the same conditions with (i) the nucleic acid sequence of SEQ ID NO:1, (ii) the cDNA sequence of SEQ ID NO:1, (iii) a subsequence of (i) or (ii), or (iv) a complementary strand of (i), (ii), or (iii); or allelic variants thereof (Sambrook et al., 1989, supra), as defined herein.

The present invention also relates to isolated nucleic acid sequences produced by (a) hybridizing a DNA under low, medium, high, or very high stringency conditions with (i) the nucleic acid sequence of SEQ ID NO:1, (ii) the cDNA sequence of SEQ ID NO:1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence that encodes a polypeptide fragment, which has cyclohexadepsipeptide synthetase activity.

The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of the mature polypeptide contained within SEQ ID NO:2 or a fragment thereof that has cyclohexadepsipeptide synthetase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

The present invention also relates to nucleic acid constructs, recombinant expression vectors, and host cells containing the nucleic acid sequence of SEQ ID NO:1, subsequences or homologues thereof, for expression of the sequences. The constructs and vectors may be constructed as described herein. The host cell may be any cell suitable for the expression of the nucleic acid sequence.

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. In a more preferred embodiment, the fungal host cell is a yeast cell or a filamentous fungal cell.

In an even more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another even more preferred embodiment, the filamentous fungal host cell is an *Acremonium, Aspergillus, Fusarium, Humicola, Mucor, Myceliophthora, Neurospora, Penicillium, Thielavia, Tolypocladium,* or *Trichoderma* cell.

In a most preferred embodiment, the filamentous fungal host cell is an *Aspergillus awamori, Aspergillus foetidus, Aspergillus japonicus, Aspergillus nidulans, Aspergillus niger Aspergillus oryzae, Fusarium bactridioides, Fusarium crookwellense* (synonym of *Fusarium cerealis*), *Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides, Fusarium venenatum,* (e.g., *Fusarium venenatum* (Nirenberg sp. nov.), *Humicola insolens, Humicola lanuginosa, Mucor miehei, Myceliophthora thermophilum, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Fusarium* host cells are described herein. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75:1920.

The present invention also relates to methods for producing a cyclohexadepsipeptide synthetase of the present invention comprising (a) cultivating a strain, which in its wild-type form is capable of producing the cyclohexadepsipeptide synthetase, to produce a supernatant comprising the cyclohexadepsipeptide synthetase; and (b) recovering the cyclohexadepsipeptide synthetase. Preferably, the strain is of the genus *Fusarium*, and more preferably *Fusarium venenatum*.

The present invention also relates to methods for producing a cyclohexadepsipeptide synthetase of the present invention comprising (a) cultivating a host cell under conditions conducive for production of the cyclohexadepsipeptide synthetase; and (b) recovering the cyclohexadepsipeptide synthetase.

In the production methods of the present invention, the cells are cultivated in a nutrient medium suitable for production of the cyclohexadepsipeptide synthetase using methods known in the art as described herein. The cyclohexadepsipeptide synthetase may be detected using methods known in the art specific for the enzyme (see, e.g., Visconti et al., 1992, supra). The resulting cyclohexadepsipeptide synthetase may be recovered and purified by methods known in the art as described herein.

The present invention also relates to methods for producing cyclohexadepsipeptides and to cyclohexadepsipeptides produced by the cyclohexadepsipeptide synthetases of the present invention. The production of a cyclohexadepsipeptide may be accomplished with the isolated synthetase or by fermentation of a cell containing the gene encoding the synthetase (see, for example, Madry et al., 1983, *European Journal of Applied Microbiology and Biotechnology* 17: 75–79). The cell may be a wild-type cell or a recombinant cell. The cyclohexadepsipeptides may be isolated and purified by any of the methods known in the art. See, for example, U.S. Pat. No. 5,656,464; Visconti et al., 1992, supra.

In a preferred embodiment, the method for producing a cyclohexadepsipeptide, comprises: (a) reacting a cyclohexadepsipeptide synthetase of the present invention with D-2-hydroxyisovaleric acid, a branched chain L-amino acid, S-adenosylmethionine, and ATP; and (b) isolating the cyclohexadepsipeptide from the reaction.

In another preferred embodiment, the method for producing a cyclohexadepsipeptide, comprises: (a) cultivating a cell under conditions suitable for the production of the cyclohexadepsipeptide, wherein the cell comprises a nucleic acid sequence encoding (i) a cyclohexadepsipeptide synthetase having an amino acid sequence which has at least 65% identity with the mature polypeptide contained within SEQ ID NO:2; (ii) a cyclohexadepsipeptide synthetase which is encoded by a nucleic acid sequence which hybridizes under medium stringency conditions with the nucleic acid sequence of SEQ ID NO:1 or its complementary strand, or a subsequence of SEQ ID NO:1 of at least 100 nucleotides; (iii) an allelic variant of (a) or (b); or (iv) a fragment of (a), (b), or (c) that has cyclohexadepsipeptide synthetase activity; and (b) isolating the cyclohexadepsipeptide from the reaction.

The present invention is further described by the following examples which should not be construed as limiting the scope of the invention.

EXAMPLES

Strains

*Fusarium venenatum* strain ATCC 20334 was used as the source of genomic DNA for these experiments. Genomic DNA libraries were constructed using the λZipLox cloning system (Life Technologies, Gaithersburg, Md.) with *E. coli* Y1090ZL as a host for plating and purification of recombinant bacteriophage and *E. coli* DH10Bzip for excision of recombinant pZL1-derivatives. *Fusarium torulosum* R-5690 (Fusarium Research Center, Penn State University, State College, Pa.) and *Aspergillus niger* Bo-1 (Novo Nordisk A/S, Bagsvaerd, Denmark) were used as sources of control DNAs for hybridization experiments. The tri5-deleted *Fusarium venenatum* strain LyMC1A (WO 99/60137) was used as the recipient for transformation experiments. *Escherichia coli* TOP10 (Invitrogen Corp., Carlsbad, Calif.) and *E. coli* DH5-alpha strains (Gibco-BRL Life Technologies, Bethesda, Md.) were used for vector construction and routine plasmid propagation.

Media

RA sporulation medium was composed per liter of 50 g of succinic acid (disodium salt), 20 ml of 50× Vogels salts, 12.1 g of $NaNO_3$, and 1 g of glucose.

50× Vogels Salts was composed per liter of 125 g of sodium citrate, 250 g of $KH_2PO_4$, 10 g of $MgSO_4.7H_2O$, 5 g of $CaCl_2.2H_2O$ (predissolved in 20 ml water), and 5 ml of 200× Vogels trace elements. (Each ingredient was dissolved completely before addition of the next one). Filter sterilized.

200× Vogels Trace Elements was composed per 100 ml of 5 g of citric acid.$1H_2O$, 5 g of $ZnSO_4.7H_2O$, 1 g of $Fe(NH_4)_2(SO_4)_2.6H_2O$, 0.25 g of $CuSO_4.5H_2O$, 0.05 g of $MnSO_4.1H_2O$, 0.05 g of $H_3BO_3$, and 0.05 g of $Na_2MoO_4.2H_2O$.

Fluoroacetamide agar (FA) was composed per liter of 12 g of sodium acetate, 2 g of sodium chloride, 0.5 g of $MgSO_4$, 3 g of $KH_2PO_4$, 0.3 g of urea, 2 g of fluoroacetamide, 1 ml of Vogels salts, and 15 g of Noble agar (pH 6.1).

Cove medium was composed per liter of 342.3 g of sucrose, 20 ml of 50× Cove salt solution, 10 ml of 1 M acetamide, 10 ml of 1.5 M CsCl, and 25 g of Noble agar.

50× Cove Salts was composed per liter of 26 g of KCl, 26 g of $MgSO_4.7H_2O$, 76 g of $KH_2PO_4$, and 50 ml of 20× Cove trace elements.

20× Cove trace elements was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

Example 1

Genomic DNA Extraction of *Fusarium venenatum*, *Fusarium torulosum*, and *Aspergillus niger*

*Fusarium venenatum*, *Fusarium torulosum*, and *Aspergillus niger* were each grown for 24–36 hours at 28° C. and 150 rpm in 25 ml of YEG medium composed per liter of 5 g of yeast extract and 20 g of glucose. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and each powder was added to 20 ml of TE buffer and 5 ml of 20% w/v sodium dodecylsulfate (SDS) in a disposable plastic centrifuge tube. The mixtures were gently inverted several times to ensure mixing, and extracted twice with an equal volume of phenol:chloroform:isoamyl alcohol (25:24:1 v/v/v). Sodium acetate (3 M solution) was added to give a final concentration of 0.3 M and the nucleic acids were precipitated with 2.5 volumes of ice cold ethanol. The tubes were centrifuged at 15,000×g for 30 minutes and the pellets were allowed to air dry for 30 minutes before resuspension in 0.5 ml of TE buffer. DNase-free ribonuclease A was added to a concentration of 100 μg/ml and the mixtures were incubated at 37° C. for 30 minutes. Proteinase K (200 μg/ml) was then added and the mixtures were incubated an additional hour at 37° C. Finally, the mixtures were extracted twice with phenol:chloroform:isoamyl alcohol (25:24:1 v/v/v) before precipitating the DNA with sodium acetate and ethanol according to standard procedures. The DNA pellets were dried under vacuum, resuspended in TE buffer, and stored at 4° C.

Example 2

Hybridization Experiments

The genomic DNA preparations described in Example 1 were tested for the presence of cyclohexadepsipeptide synthetase gene sequences using Southern hybridization. Aliquots of the DNA were digested with BamHI or BamHI plus XbaI and fractionated by agarose gel electrophoresis. The DNA in the gel was blotted to a Hybond N+™ membrane filter (Amersham Corporation, Arlington Heights, Ill.) according to the method of Davis et al. (1980, *Advanced Bacterial Genetics, A Manual for Genetic Engineering*, Cold Spring Harbor Press, Cold Spring Harbor, N.Y.), and probed with a radiolabeled fragment encoding the 5' portion of the *Fusarium torulosum esyn1* gene (obtained from Dr. Thomas Hohn, USDA, Peoria, Ill.) under low, medium, and high stringency hybridization conditions at 45° C. as described herein. The cyclohexadepsipeptide synthetase-specific probe fragment from *Fusarium torulosum* was radiolabeled by nick translation (Sambrook et al., 1989, *Molecular Cloning. A Laboratory Manual*, Cold Spring Harbor Press, Cold Spring Harbor, N.Y.) with α[$^{32}$P]dCTP (Amersham, Arlington Heights, Ill.), denatured by adding NaOH to a final concentration of 0.1 M, and added to the hybridization buffer at an activity of approximately $1\times10^6$ cpm per ml. Following the hybridization, the filters were washed once in 0.2×SSPE with 0.1% SDS at 45° C. followed by two washes in 0.2×SSPE (no SDS) at the same temperature. The filters were allowed to dry on paper towels for 15 minutes, then wrapped in Saran-wrap™ and exposed to X-ray film overnight at −70° C. with intensifying screens (Kodak, Rochester, N.Y.).

Southern hybridization analysis showed that cyclohexadepsipeptide synthetase-specific DNA sequences could be detected in the genome of *Fusarium venenatum* with the *Fusarium torulosum esynl* probe only under conditions of low and medium stringency. The positive control DNA from *Fusarium torulosum* gave strong hybridization signals under all conditions, and negative control DNA from *Aspergillus niger* failed to hybridize under all conditions tested. These results suggested that *Fusarium venenatum* contained genomic DNA sequences homologous to the *Fusarium torulosum* enniatin synthetase gene.

Example 3

Genomic DNA Library Construction and Screening

Genomic libraries of *Fusarium venenatum* were constructed in λZipLox according to the manufacturer's instructions (Life Technologies, Gaithersburg, Md.). *Fusarium venenatum* genomic DNA was partially digested with Tsp509I and size-fractionated on 1% agarose gels. DNA fragments migrating in the size range 3–7 kb were excised and eluted from the agarose gel slices using Prep-a-Gene reagents (BioRad, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *E. coli* Y1090ZL cells.

Approximately 50,000 plaques from the library were screened by plaque-hybridization (Davis et al., 1980, supra) with the radiolabeled probe fragment of the *Fusarium torulosum esyn1* gene using the low stringency conditions described in Example 2. Plaques, which gave hybridization signals, were purified twice in *E. coli* Y 1090ZL cells, and the individual clones were subsequently excised from the λZipLox vector as pZL1-derivatives (D'Alessio et al., 1992, Focus® 14: 7). Chromosome "walking" to obtain adjacent DNA sequences was done using homologous *Fusarium venenatum* probes at high stringency.

Four plaques were identified that hybridized strongly to the *Fusarium torulosum esyn1* gene probe, and each of the potential clones was subsequently excised from the λZipLox vector as a pZL1-derivative (D'Alessio et al., 1992, supra). Plasmid DNA was isolated from the clones by passage through *E. coli* DH10B cells using standard methods. The sizes of the cloned inserts were determined by agarose gel electrophoresis. The largest insert comprised a DNA segment of approximately 3 kb. The clone was designated *E. coli* DH10B pZL-ESA.

Example 4

Cloning and Analysis of a *Fusarium venenatum* Cyclohexadepsipeptide Synthetase Gene DNA sequencing of the DNA segment of approximately 3 kb was performed with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.). The entire cloned region was sequenced to an average redundancy of 6.9.

Nucleotide sequencing revealed that the 3 kb segment contained an open reading frame encoding at least 900 amino acids. However, this fragment (designated Fragment A, pZL-ESA) did not encode the entire gene product. Consequently, the library was re-screened using a probe comprising the 3'-portion of Fragment A (ca. 1 kb HindIII fragment). Several clones were subsequently identified and analyzed by restriction mapping. The largest of these secondary clones contained a genomic DNA insert of about 4.6 kb (designated Fragment B, pZL-ESB). The clone was designated *E. coli* DH10B pZL-ESB.

Nucleotide sequence examination of Fragment B extended the open reading frame of Fragment A by amino acids 777 through 2311. However, this sequence did not reach the stop codon of the open reading frame, thereby necessitating isolation of a third genomic segment. The third genomic clone was isolated by re-screening the genomic library with a PCR-amplified probe derived from Fragment B. Two PCR primers shown below were used to amplify a 586 bp probe segment used for screening the library.

5'-dAATTGATTCGCTTGAAAGTCGAT-3' (SEQ ID NO:3)

5'-dCTTGAGAGTTACGTTGGTCTTGAAC-3' (SEQ ID NO:4)

The amplification reaction (100 µl) contained the following components: 0.2 µg of pZL-ESB DNA, 48.4 pmol of the forward primer, 48.4 pmol of the reverse primer, 1 mM each of dATP, dCTP, dGTP, and dTTP, 1×Taq polymerase buffer, and 2.5 U of Taq polymerase (Perkin-Elmer Corp., Branchburg, N.J.). The reaction was incubated in an Ericomp Twin Block System Easy Cycler programmed for 1 cycle at 95° C. for 5 minutes followed by 30 cycles each at 95° C. for 1 minute, 55° C. for 1 minute and 72° C. for 2 minutes.

The reaction was electrophoresed on an agarose gel, and the expected product of 586 bp was obtained. The reaction was run on a preparative gel, a gel slice containing the desired product was excised, and DNA was isolated from the gel using a Qiaquick Gel Extraction Kit (Qiagen, Chatsworth, Calif.).

From seven clones that were identified with this probe, the largest (fragment C, pZL-ESC) contained a 5.5 kb insert. Subsequent DNA sequence analysis revealed that Fragment C encoded amino acids 1617 through 3129, a potential stop codon, and 1553 bp of 3'-flanking DNA. The clone was designated *E. coli* DH10B pZL-ESC. The entire DNA sequence of the cyclohexadepsipeptide synthetase gene was assembled from the three overlapping clones (Fragments A, B, and C). A transposon insertion strategy allowed for rapid sequencing to high redundancy.

The complete DNA sequence and deduced amino acid sequence are shown in FIG. 1. The DNA sequence of the cyclohexadepsipeptide synthetase gene (SEQ ID NO:1) was determined to an average redundancy of 6.9. The cyclohexadepsipeptide synthetase gene contained a lengthy open reading frame of 9387 bp with no introns, encoding a polypeptide of 3129 amino acids (MW=346,852).

The deduced amino acid sequence (SEQ ID NO:2) of the cyclohexadepsipeptide synthetase gene product shared approximately 59% identity to the enniatin synthetase of *Fusarium scirpi* (Haese et al., 1993, *Mol. Microbiol.* 7: 905–914; DNA sequence listed in EMBL database under accession number Z18755). Percent identity was determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Example 5 pΔES-amdS Construction

The construction of the dps1 deletion vectors pΔES-amdS1 and pΔES-amdS2 is shown in FIG. 2. Briefly, a 0.2 kb DNA segment comprising a portion of the dps1 coding region was removed from plasmid pZL-ESA (designated as fragment A) by digestion with StuI and NruI restriction endonucleases. Both of these enzymes generate blunt-ended DNA fragments. The digested pESA vector was treated with calf intestine alkaline phosphatase (Boehringer-Mannheim Biochemicals, Indianapolis, Ind.) to prevent self-ligation. Lastly, a 3.2 kb fragment encoding the *Aspergillus nidulans* amdS gene (with flanking repeat sequences derived from the *Aspergillus oryzae* pyrG gene) was obtained by digestion of pJRoy47 (WO 99/60137) with SmaI and PmeI. This amdS fragment was subsequently ligated with the pZL-ESA vector fragment described above to generate the deletion plasmids pΔES-amdS1 and pΔES-amdS2 (which differ only in the orientation of the amdS gene segment).

Example 6

Transformation of *Fusarium venenatum* LyMC1A and Preliminary Screening for dps1 Gene Deletions Plasmid pΔES-amdS1 was digested with SpeI, and the 5.7 kb deletion fragment (comprising portions of the *Fusarium* venenatum dps1 gene with the *Aspergillus nidulans* amdS gene and repeats replacing 0.2 kb of the dps1 coding region) was subsequently excised and purified for use in transformation experiments. The preparation and transformation of *Fusarium venenatum* LyMC1A protoplasts was performed according to the method of Royer, 1995, *Bio/Technology* 13: 1479–1483.

*Fusarium venenatum* LyMC1A protoplasts were transformed with the 5.7 kb SpeI ΔES-amdS fragment with selection on COVE plates. Fifteen transformants were obtained and single spore purified. DNA was extracted from the single spore purified transformants, generated with the SpeI ΔES-amdS fragment, as well as from *Fusarium venenatum* LyMC1A, using the Qiagen DNeasy Plant mini kit (Qiagen, Chatsworth, Calif.) (with a 2 hour lytic incubation in place of 10 minutes recommended in the manufacturer's protocol). One to two micrograms of each DNA were digested for seven hours with XhoI or SpeI (10 U/µg DNA in 30 µl reactions). The digests were electrophoresed on 1% agarose gels in TAE buffer, and the DNAs were transferred to Hybond N+ in 0.4 N NaOH. The blots were UV crosslinked and probed as described below.

Probes were prepared using the Prime-It Labeling Kit (Stratagene, La Jolla, Calif.) and α[$^{32}$P]-dCTP. Following labeling the probes were separated from unincorporated label using a G 50 TE Midi column (5' to 3', Boulder, Colo.).

Blots were prehybridized at 65° C. in Rapid Hyb Buffer (Amersham, Arlington Heights, Ill.) for 45 minutes. Denatured probes were added to the Rapid Hyb solution and hybridizations were done overnight at 65° C. Following hybridization the blots were washed once at room temperature in 2×SSC for 5 minutes and in 0.2×SSC, 0.1% SDS at 65° C. for 5 minutes twice. The washed blots were washed in 2×SSC at room temperature for 5 minutes.

Southern blots of XhoI and SpeI-digested genomic DNA were probed twice. First, they were probed with an 800 bp NsiI/SpeI fragment of p≠ES-amdS1. Four of the fifteen transformants had the 5.2 kb band (XhoI digested DNA) and the 5.7 kb band (SpeI digested DNA) expected for a gene replacement when probed with the 800 bp NsiI/SpeI fragment. Most of the other transformants had the 2.2 kb band (XhoI digested DNA) or the 2.7 kb (SpeI digested DNA) wild-type bands, and additional bands, most likely corresponding to ectopic integration of the transforming DNA.

Secondly, the same Southern blots were probed with HindIII-linearized pDSY176, a plasmid containing the 0.2 kb StuI/NruI portion of the dps1 coding region. pDSY176 was constructed as follows: pZL-ESA was digested with StuI/NruI, and the 0.2 kb fragment was isolated by preparative electrophoresis. The isolated fragment was cloned into pZERO-Blunt (Invitrogen Corp., Carlsbad, Calif.) according to the manufacturer's instructions to produce pDSY176. Hybridization analysis using this second probe (pDSY176) confirmed that none of the four putative deleted strains (*Fusarium venenatum* ΔES 4, 6, 8, and 10) contained the 0.2 kb region of the dps1 gene which had been deleted.

Example 7

Removal of the amdS Gene

Two of the transformants confirmed as being deleted, ΔES4A and ΔES8A, were sporulated in 500 ml of RA medium, in 2 liter Fernbach flasks. These were inoculated with 12 mycelial plugs cut from Cove plates and incubated at 24° C., 150 rpm for 53 hours. After this time spores were harvested through sterile Miracloth (Calbiochem, San Diego, Calif.) centrifuged for 30 minutes at 7,000 rpm in a Sorval GS3 rotor and washed three times with sterile water. Freshly harvested spores were plated at $10^4$, $10^5$ and $10^6$ per plate (five plates at each concentration) of FA. Colonies which grew on these plates were picked to FA and Cove plates.

Numerous colonies were obtained on FA plates (primarily from plates seeded with $10^5$ and $10^6$ spores/plate) which, on subculturing, grew well on FA but only sparsely on Cove. Thirty two ΔES4A-derived colonies (designated as *Fusarium venenatum* WTY700-3-4) and 128 ΔES8A-derived colonies (designated as *Fusarium venenatum* WTY700-3-8) all had an amdS-minus phenotype.

DNA was extracted from five *Fusarium venenatum* WTY700-3-4 isolates (WTY700-3-4a through 4e) and ten *Fusarium venenatum* WTY700-3-8 strains (WTY700-3-8a through 8j) as well as LyMC1A, ΔES4A and ΔES8A using the Qiagen DNeasy Plant Mini Kit (with a 2 hour lytic incubation in place of 10 min recommended in the manufacturer's protocol). One microgram of each DNA was digested overnight with XhoI and SpeI (20 U/μg DNA in 50 μl reactions). The digests were concentrated to 10 μl and run on 1% agarose gels in TBE. DNAs were transferred to Hybond N+ membranes using the manufacturer's protocol, and were then probed with the probes described in Example 6.

Hybridization analysis of genomic DNAs extracted from these strains (using the 800 bp NsiI-SpeI fragment of ΔES-amdS1 and HindIII-digested pDSY176 (which contains the 200 bp StuI-NruI portion of the dps1 open reading frame) revealed that none of the WTY700-3-4 isolates had lost the amdS gene, but 50% (5/10) of the *Fusarium venenatum* WTY700-3-8 isolates showed a banding pattern consistent with removal of the amdS gene. Hybridization analysis, thus, confirmed that *Fusarium venenatum* WTY700-3-8a, b, c, d, and e were deleted for the 200 bp StuI-NruI portion of the dps1 open reading frame. As expected for a deletion, a hybridization signal was observed using the pDSY176 probe described above for the parent strain *Fusarium venenatum* LyMC1A but not for any of the five *Fusarium venenatum* WTY700-3-8a-e strains.

Deposit of Biological Materials

The following biological materials have been deposited under the terms of the Budapest Treaty with the Agricultural Research Service Patent Culture Collection, Northern Regional Research Center (NRRL), Peoria, Ill., and given the following accession numbers:

| Deposit | Accession Number | Date of Deposit |
|---|---|---|
| *E. coli* DH10B (pZL-ESA) | NRRL B-30068 | Oct. 27, 1998 |
| *E. coli* DH10B (pZL-ESB) | NRRL B-30069 | Oct. 27, 1998 |
| *E. coli* DH10B (pZL-ESC) | NRRL B-30070 | Oct. 27, 1998 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

SEQUENCE LISTING

<160> NUMBER OF SEQ ID NOS: 4

<210> SEQ ID NO 1
<211> LENGTH: 11212
<212> TYPE: DNA
<213> ORGANISM: Fusarium

<400> SEQUENCE: 1

```
aattagattc cactagtacg ccattgtaga atcaaggcca agatatgaac aacccataag      60
taacggcgat cctgtctcat gtatccaaaa ataagagaca cggcatattc actgctttgc     120
agatctttct tcaaatctct ccctcgagaa gctactggga tgaatgagtc tcttggctca     180
gattagatat attcactgta tctgccgaat agactttgcc tggtagcatt aacgttccta     240
tattctatta tcaaatcctt acattcaata tggaatatct tactgctgtc gatggtaggc     300
aagacctgcc acctacacca gcttcgtttt gtagtcatgg agatagtccc ctcaatagct     360
cttacgagca actcttccat ctctatggtc tggattcgag tcgcatcgaa gctatcaaac     420
catgcacacc tttccagctt gacatgatcg actgcaatgc tttggataag cagtctgcta     480
tcggccatgc ggtgtatgat gtcccaaccg acattgacat ctctcgtttc gcgcttgcgt     540
ggaaggagat cgtcaaccaa accccagcct tgcgagcctt tgccttcacc tcggactctg     600
gaaagacttc tcaagtcatc ctaaaagata gctttgtctt ctcatggatg tgctggtctt     660
cttcgagctc cccagatgaa gtggttcggg atgaagctgc cgctgctgca tccgggccac     720
gctgcaaccg cttcgttcta cttgaagaca tgcagacgaa gaaatgtcag ctggtttgga     780
ccttcagtca tgcattggta gacgtcactt tccaacaacg cgtcctgagc cgtgttttcg     840
cggcttacaa gcatgagaag gacacacatc ggcctgagac acccgagtca tctgatgcca     900
ctgacactga ctctcagtca gtctccgtgg tgtccatgag ctgcgaggac aatgccgtat     960
cggcgactca tttctggcaa actcacctta acgatctcaa tgcgtccgtc ttccctcacc    1020
tgtctgacca cctgatggtg cccaacccaa ctacaacagc agagcatcgt atcacattcc    1080
ctctttcaca gaaagcacta tccaattctg ccatctgccg tactgcactc tcaatactcc    1140
tctcgcgcta cactcactct gacgaggcct tgtttggtgc ggtaactgag caatctctac    1200
catttgacaa acactatctt gcagatggta cgtaccaaac agttgcaccc cttcgtgtac    1260
actgccaatc aaatcttcgt gcatcagatg tcatggatgc aatctcttct tacgatgatc    1320
gccttggtca tctcgcccca tttggccttc gcgacatccg caacactggt gataatggct    1380
ctgccgcctg cgatttccaa actgttttac tcgtcaccga tggcagccac gtaaacaatg    1440
gtatcaacgg tttcctccaa cagataacag agtcaagcca tttcatgcct tgcaacaacc    1500
gtgccctcct tctgcactgt cagatggaaa gtagcggagc tctgctggtt gcctactatg    1560
accacaatgt tatcgattcg cttcagacaa cgcgtctgct acagcagttt ggtcatctga    1620
tcaagtgttt gcaaagtcct ctagacctga gctctatggc tgaggtcaac ttgatgactg    1680
```

-continued

```
agtatgacag agcagagatt gagagttgga actcgcaacc gttagaggta caggataccc    1740
tgatccacca tgagatgttg aaagctgttt ctcattcccc caccaaaacg gccatccaag    1800
cgtgggatgg agactggacc tattccgagc tcgacaatgt ttcgtcaaga ctcgctgtcc    1860
atatcaagtc acttggcctt agagctcagc aagccattat tccagtctac tttgagaagt    1920
cgaaatgggt cattgcttca atgctggctg ttctcaagtc tggtaatgct ttcactctaa    1980
ttgatcccaa tgatccacca gctcgaactg cccaggtcgt cacgcagact cgggcgactg    2040
tagcgcttac ttccaagcta caccgcgaga ctgtacagaa gcttgtaggc cgttgcgttg    2100
tggttgatga cgagcttctg caatcagttt ctgccagcga cgatttctca agtctgacca    2160
aatcgcaaga cttggcctac gtgatcttca cttctggtag cacgggcgac ccgaaaggca    2220
tcatgattga acaccgagcg ttctcatcat gtgcactcaa gttcggcgcg tctcttggca    2280
tcaactctga tactcgtgcc ctacaatttg gaacccatgc cttttggcgca tgtcttctcg    2340
agattatgac tactctcatc aacggtggct gcgtttgtat tccctccgac gatgatcgta    2400
tgaacagtat cccgtccttc atcaaccgat acaacgttaa ttggatgatg gcgacacctt    2460
cgtacatggg aaccttttca cctgaagacg ttcctggcct tgcgacattg gtacttgttg    2520
gggagcagat gtcatcttca gtcaacgcaa tctgggcccc caagctccaa ctcttgaacg    2580
ggtacggaca gagtgaaagt tcctcaattt gttttgcctc caatatgtca actgagccca    2640
acaacatggg cagagcagtc ggagctcatt catgggtcat tgacccgaac gatataaacc    2700
gactagttcc gattggagct gtgggagaac tggtcattga gagtccaggc attgcccgcg    2760
actacattgt tccccccct ccggagaagt ccccattctt cacagacatt ccaagctggt    2820
atccagcgaa cacgtttcct gatggggcaa aactctacag gacaggagat cttgcaagat    2880
atgcctccga tgggtccatc gtttgccttg ggcgcataga ctcgcaggtc aagatccggg    2940
gacagcgtgt tgagctgggt gccattgaga cccatctccg acagcagatg ccagacgact    3000
tgactattgt ggtagaagct accaagcgat cccaatctgc caacagcaca tccttaattg    3060
cattcctaat agggtcttct tacttcggaa atagaccctc ggatgcccac attctggacc    3120
atgatgctac caaagctatc aacataaagc tggagcaggt attgcctcga cactctatcc    3180
cctcattcta catctgcatg ctggagcttc cacgtactgc caccgggaag atagatagga    3240
ggcgactacg aatcatgggc aaagacatct tggacaagca gacccaaggg gccattgttc    3300
aacaagcacc cgctcctatc cctgttttcg cagacacagc agcaaagctc cacagtatct    3360
gggtacagag tttgggtatc gatccagcca cggtcaatgt tggggcaact ttcttcgaac    3420
tcggaggaaa ctctatcact gctatcaaga tggtgaacat ggcgaggtcc gttggtatgg    3480
acctcaaggt ctctaacatc taccagcacc cgacgcttgc gggaatttcc gcggtcgtca    3540
agggtgatcc tctgtcctac actctcatcc ccaagtcaac tcatgaggga cctgttgagc    3600
agtcttattc acaaggccga ctatggttcc tggatcagtt ggacgttggc agtctgtggt    3660
atctgattcc atatgctgtg agaatgcgcg ggcctgtcaa tgtcgacgcg ttacgtcggg    3720
ctcttgcagc gcttgaacag cgacacgaga ctcttagaac gacatttgaa gaccaggatg    3780
gtgtcggtgt acaaattgtt cacgagaagc tttctgagga gatgaaggtc attgatctct    3840
gtggttcaga ccttgacccg tttgaggtgt tgaaccaaga acagactact cccttcaatc    3900
tctcatctga agctggctgg agagcgacgc tcttacgact tggtgaagat gaccacatcc    3960
tcactattgt catgcatcac atcatctcag atggttggtc aattgatgtc ttgcgacgcg    4020
```

-continued

```
atctcaatca gctctactca gctgcgctca aggactcaaa agacccgctg tcagcactca    4080
ctcctctacc tatccagtac agcgactttg caaaatggca gaaggaccaa ttcatagagc    4140
aggagaagca actcaactac tggaagaagc aactcaaaga ctcttcccca gcaaagatcc    4200
cgaccgactt tgcccgccct gcacttctgt ctggagacgc aggttgcgta catgttacca    4260
tcgacggcga gctctaccag tcccttcgag ccttctgcaa cgaacacaac acgacctctt    4320
tcgtcgttct tctagctgcg ttccgtgccg ctcattatcg tctcacagct gttgaagacg    4380
ctgtcattgg tacaccaatt gcgaatcgca accgacctga actggaggat atcatcggct    4440
gctttgtcaa tacgcagtgt atgcgaatca acatagatca tcacgatacc tttgggactt    4500
tgatcaacca agtcaaggct acgacgacag cagcattcga gaacgaggat attccgtttg    4560
agcgcgttgt atcagcacta cagcctggat ccagagatct gtcaagcaca cctctcgcac    4620
aactcatttt tgcagtgcac tcacagaagg accttggaag attcaagttc cagggtctcg    4680
agtccgtacc tgtgcctagc aaagcgtaca ctcgatttga catggagttc catctgtttc    4740
aagaaaccga cagccttaaa ggtagcgtca actttgccga tgagctgttc aaaatggaga    4800
ctgttgaaaa tgtcgtcaga gtattctttg agattctgag aaacgggctt caaagttcgc    4860
ggacaccagt ctcaatactt cctttgactg atggcattgt gactcttgaa aaattggatg    4920
ttctcaacgt caaacatgtc gactatcccc gagaatcgag cttggctgat gtcttccaga    4980
cccaagtctc tgcttacccc gatagtctgg ctgtggtgga ctcctcgtgc cgattgacct    5040
acaccgagtt ggatcgccag tctgatattc tcgctggatg gcttcgtcga cggtcaatgc    5100
ctgcagagac gcttgtcgca gtatttgccc cacggtcatg tgagacaatt gtcgcgttct    5160
ttggtgtgtt gaaggcgaac ttggcctatc ttcctctcga tgtacgatcg ccctcggcga    5220
gagttcagga tatactttct ggactttctg ggcctaccat tgttttgatt ggccatgata    5280
cagcgcctcc cgatatcgag gttactaacg tcgagtttgt tcgtatccgg gatgcgctga    5340
atgacagcaa tgcagatggc tttgaagtca tcgagcacga cagcacaaag ccctcagcca    5400
cgagtctcgc atacgtgctg tatacctcag gatccactgg ccgaccaaaa ggcgtcatga    5460
ttgagcaccg tgtcattatt cgaacagtca caagtggctg tatacccaac tatccttcgg    5520
aaacgaggat ggctcacatg gcgaccattg cgtttgacgg cgcatcgtac gagatctaca    5580 gcgcccttt tgttcggaagg acacttgttt gcgttgacta catgacaacc ctcgacgcta    5640
gagcactcaa ggatgtgttt ttccgagagc atgtcaacgc ggcaagtcat gtcaccagct    5700
cttctcaaga tgtacctctc cgagtcccga gaaggctctc gagaaccttg atgttcttct    5760
tcttggtggt gacagattcg acggcccag atgctctcga tgcgcaggga ctttatcaag    5820
gggtccagtg ttacaatggt tacggcccaa cagagaatga agtcatgagt acaatctatc    5880
ccattgactc gactgagtcg ttcatcaatg gagtcccaat tggacgagct ctgaacaact    5940
caggagcgta tgtcgtggat cctgagcaac agcttgttgg cattggtgtg atgggagagc    6000
ttgttgtcac tggcgatggt cttgcgcggg gctacagtga caaagcccct gacgagaacc    6060
gttttgtgca cattactgtc aatgaccaga cagtgaaggc gtatcgcact ggcgatcgag    6120
tgcggtacag gattggagat ggcctcatcg agttcttcgg acgtatggac acccagttca    6180
agattcgtgg caatcgtatc gaatcagctg agattgaagc ggcccttctg cgcgactcct    6240
ccgtccgaga tgctgctgtc gtccttcagc agaatgagga tcaagcgcct gagatcttgg    6300
ggtttgttgt tgctgatcat gatcattctg agaatgacaa gggacaatct gccaatcaag    6360
tcgaaggatg gcaagaccat ttcgagagtg gcatgtattc cgacattggc gaaattgacc    6420
```

```
cgtcgacgat tggtagcgac ttcaagggtt ggacatcaat gtatgatgga agtcaaatcg    6480
acttcgatga gatgcacgag tggcttggtg agactacccg gacactccat gacaatcgct    6540
ctctaggcaa tgtccttgaa attggaacag gtagcggcat gatcctcttc aaccttgaca    6600
gcaggcttga gagttacgtt ggtcttgaac catccagatc agcagctgca tttgtcaaca    6660
aagctaccga gtctatacca tcgcttgctg gaaaagccaa ggttcaggtt ggaacagcta    6720
cagatattgg tcaagtcgat gacttacacc ctgacctcgt ggttctcaac tcagtcattc    6780
agtatttccc gtcttcggag taccttgcag aaatcgcaga caccttgatt catctgccta    6840
acgtgcagcg gattttcttt ggcgatgtcc gatcgcaggc caccaacgag cacttccttg    6900
ctgccagggc tatccacaca ctggggaaga atgcaacgaa ggacgatgtt cgacagaaaa    6960
tggcagaatt ggaggacatg gaggaggagt tgcttgttga acctgctttc ttcacctcgt    7020
tgaaagacag gtttccaggt ctggtggaac atgttgagat cctgccaaag aacatggaag    7080
ctgtgaatga gctcagtgcg tatcgatatg ccgctgttgt gcacgttcgg ggttcacttg    7140
gagatgagct tgtgcttccg gttgagaaag atgactggat cgactttcaa gcgaatcaat    7200
tgaaccagaa gtcactgggt gaccttctca gtcttcaga tgctgctatc atggcagtca    7260
gcaaaattcc tttcgaaatc acggcctttg aaagacaggt cgtcgcttcc ctcaatagca    7320
acatcgatga gtggcagcta tcaaccattc ggtccagcgc cgagggcgac tcatcactat    7380
ccgttcccga catctttcgc attgctgggg aagccgggtt ccgtgtcgag gtcagttctg    7440
cacgacagtg gtctcagaat ggtgcattgg acgctgtttt ccatcattgt tgctcccaag    7500
ggcgtactct ggtcaacttt cctacggacc atcaccttcg agggtctgat ctcctcacca    7560
atcgacccct tcagcgactg caaaaccgtc gtatcgccat cgaagtccgc gagaggcttc    7620
ggtccttact tccatcgtac atgatcccat cgaacatcgt tgttctggac aagatgcctc    7680
tcaacgccaa tggtaaagtt gaccggaagg aactctctcg cagggcaaag gttgtaccga    7740
agcagcagac agcagcgccg ttaccgacat ttcccatcag tgaggtcgaa gtcattcttt    7800
gcgaagaagc cactgaggtg tttggcatga aggttgacat taccgatcac ttcttcaatc    7860
tcggtggaca ctctctcttg gccacgaagc tcatttctcg tatcgaccaa cgactcaagg    7920
tccgtatcac tgtcaaggat gtctttgacc atcctgtatt tgcggatcta gcatctgtca    7980
tccgtcaagg gctgggtttg caacaacccg tttctgatgg tcagggacaa gacagatctg    8040
cccacatggc acccgtacc gagactgaag ctatactctg tgatgagttt gcaaaggttc    8100
tggggttcca agtcgggatt acagacaatt tctttgatct tggtggtcat tcactcatgg    8160
ctactaaact cgctgtgcgc atcggacatc gacttgacac gactgtttcg gtgaaggatg    8220
ttttcgatca tcctgtactc ttccaacttg caattgcatt ggataacttg gttcaatcca    8280
agaccaatga gatagttgga ggtagagaaa tggctgaata ctcacctttc caactcctct    8340
ttacagaaga cccagaggag tttatggcga gcgagatcaa gccacaactt gagttacagg    8400
aaatcattca agacatatat ccgtctaccc agatgcagaa ggctttcctc ttcgatcaca    8460
caactgcgcg cccgagacct ttcgtgccgt tctacatcga cttccccagc acttccgagc    8520
ctgatgctgc aggtctaatc aaggcttgcg agtctctggt aaatcatctt gacatcttca    8580
gaacagtctt tgcagaggca tctggagaac tataccaagt ggtcttgtcc tgtccttgatc    8640 tgccaatcca agtgattgag acagaagaca acatcaatac ggcgacaaat gagtttctcg    8700
atgagtttgc gaaagagcca gttcgtctgg gacatccgtt gattcgtttt acaatcatca    8760
```

```
aacaaaccaa gtcgatgcgt gtgataatga gaatatcgca tgccctgtat gatggtctga   8820
gtctagagca tgtcgtgcgc aaacttcaca tgctctacaa cgggagatca cttttgccac   8880
cacaccaatt ctcgcggtac atgcagtata ctgctgacgg tcgcgaaagt ggacatggat   8940
tttggcgcga tgtgattcaa aatacgccca tgacaatatt gagtgatgac acggttgttg   9000
atggaaatga tgcaacctgc aaggcgttgc acctatcaaa gattgtcaat attccttcac   9060
aggtacttcg aggcagcagt aacatcatta ctcaagctac tgtgtttaac gcagcctgcg   9120
cgttagtctt gtcacgggaa tctgactcga aagacgttgt cttttggacgc atcgtctctg   9180 gtcgtcaagg cttgcctgtt gaataccagg acattgtcgg gccttgtacc aacgcagttc   9240
ctgttcgcgc tcatatagag tcgtcagatt acaaccaatt gctgcacgac atccaagacc   9300
agtaccttct cagcttgcca cacgaaacaa ttggcttctc agatctcaag cgcaactgta   9360
cagattggcc agaagcaatc accaacttct catgctgcat cacataccac aatttcgagt   9420
accatcccga gagtcagttc gaacagcaga gagttgagat gggtgtattg acaaagtttg   9480
tcaacattga gatggatgag ccactatatg atttggcgat tgcgggtgaa gttgaaccag   9540
acggagcagg actgaaggtt actgttatcg cgaagacgca gttatttggt aggaagagag   9600
tagaacatct gttggaggaa gttttccaaaa cgtttgaggg tctcaactct tctttgtaac   9660
gcacgggttg gtctcaatcg tcgcgacaga acaaccgatg taggtttgta attcttaatg   9720
acgtctttga cttttggtt tttaccattc ggagcaaata gtaagcagaa cactggcaaa   9780
tgtcagatat tacacttcag aactattatc ttgactatta tctcacgttg tcagctttca   9840
catgcttgct acgttcgatc gagtcaaaaa ttgagatcta cagggtaacg caggaatcca   9900
gaacaattga caaggattca tcgatcgaac actatgattg gttcgcgtct ctgacaggac   9960
catttgtcca ataatagaag tatagataag atatgcgagg aatgcgacaa ggattggaac  10020
tatccgagtc agcttgatct agtccctaaa cagtaaatag ctcgcgcttc ttcggattcg  10080 cttttggtgta tgaattatca tagtttgttg tgcgaagaag aacgatgatg acagcttgta  10140
ttttggatat atataagttc ataaaggtat gactcttgat atgatcaaat tagaaacaat  10200
accttgacaa tattgtgttc caacattaca caacacttga acgggacact cyttcaacat  10260
caacacaatg gatctgtcca acaaagctgc ctaccttgtc agtcccaatg ggcccaccat  10320
cgaagtcaga tctgcacctg ttccaacacc tggttcagga gagttgctta tcaagacaca  10380
tgctgtcgcc atcaatccag tcgacggagt gaagcagtcc atgggtaaca tgatgtttga  10440
atggctcaag tatcctctca tccttggcta cgatgtcgct ggcgaggtca tcaagacggg  10500
acctggtgtt agtcgattta agaaggcga tagagttgtg ggtgctacag caggcatgga  10560
caagcgagga agaagtcccg acgaaggcgc atttcaagaa gtttgcatca tgcgagagca  10620
tttggctgct cgaattccag agcgtgttac gtccaccgat gccagcgttt tgcctctgac  10680
tttcgtcacg gctgcatgtg ccttgttcca aaaggatcaa ctggcactac aactacctca  10740
aaccaagtca agcgcagtg caacaagtca gacagtcttg gtttggggag cgagtacaag  10800
tgttgggaga aatgctgtac agcttgctgt cgcggccggc tatgatgttg tcgcgacagc  10860
atcacctaag aactgggata tcgtacgcgg tctcggcgct tgtgcagttt ttgactatca  10920
cagctcatcg gccataaacg atgtggtatc tgctttcaag acaagaaat gcgcaggtgc  10980 tgtagctatt ggtcaagggt cactggcgaa atgcgtcgac attgtcaaaa gcgttccggg  11040
agccaccaag aatgttgcgc aagttaccct ctcaatgcct gagtcacagc caacaaccaa  11100
gatatccatg attccgtttg tcgcaaagta tttctggatg gcgggaactg atcgactcaa  11160
```

```
ggttgcgagc agtggagtcc aaagcaagtt tgtttttggt acagacataa tt            11212
```

<210> SEQ ID NO 2
<211> LENGTH: 3129
<212> TYPE: PRT
<213> ORGANISM: Fusarium

<400> SEQUENCE: 2

```
Met Glu Tyr Leu Thr Ala Val Asp Gly Arg Gln Asp Leu Pro Pro Thr
 1               5                  10                  15

Pro Ala Ser Phe Cys Ser His Gly Asp Ser Pro Leu Asn Ser Ser Tyr
            20                  25                  30

Glu Gln Leu Phe His Leu Tyr Gly Leu Asp Ser Ser Arg Ile Glu Ala
        35                  40                  45

Ile Lys Pro Cys Thr Pro Phe Gln Leu Asp Met Ile Asp Cys Asn Ala
 50                  55                  60

Leu Asp Lys Gln Ser Ala Ile Gly His Ala Val Tyr Asp Val Pro Thr
 65                  70                  75                  80

Asp Ile Asp Ile Ser Arg Phe Ala Leu Ala Trp Lys Glu Ile Val Asn
                85                  90                  95

Gln Thr Pro Ala Leu Arg Ala Phe Ala Phe Thr Ser Asp Ser Gly Lys
            100                 105                 110

Thr Ser Gln Val Ile Leu Lys Asp Ser Phe Val Phe Ser Trp Met Cys
        115                 120                 125

Trp Ser Ser Ser Ser Pro Asp Glu Val Val Arg Asp Glu Ala Ala
130                 135                 140

Ala Ala Ala Ser Gly Pro Arg Cys Asn Arg Phe Val Leu Leu Glu Asp
145                 150                 155                 160

Met Gln Thr Lys Lys Cys Gln Leu Val Trp Thr Phe Ser His Ala Leu
                165                 170                 175

Val Asp Val Thr Phe Gln Gln Arg Val Leu Ser Arg Val Phe Ala Ala
            180                 185                 190

Tyr Lys His Glu Lys Asp Thr His Arg Pro Glu Thr Pro Glu Ser Ser
        195                 200                 205

Asp Ala Thr Asp Thr Asp Ser Gln Ser Val Ser Val Ser Met Ser
210                 215                 220

Cys Glu Asp Asn Ala Val Ser Ala Thr His Phe Trp Gln Thr His Leu
225                 230                 235                 240

Asn Asp Leu Asn Ala Ser Val Phe Pro His Leu Ser Asp His Leu Met
                245                 250                 255

Val Pro Asn Pro Thr Thr Thr Ala Glu His Arg Ile Thr Phe Pro Leu
            260                 265                 270

Ser Gln Lys Ala Leu Ser Asn Ser Ala Ile Cys Arg Thr Ala Leu Ser
        275                 280                 285

Ile Leu Leu Ser Arg Tyr Thr His Ser Asp Glu Ala Leu Phe Gly Ala
    290                 295                 300

Val Thr Glu Gln Ser Leu Pro Phe Asp Lys His Tyr Leu Ala Asp Gly
305                 310                 315                 320

Thr Tyr Gln Thr Val Ala Pro Leu Arg Val His Cys Gln Ser Asn Leu
                325                 330                 335

Arg Ala Ser Asp Val Met Asp Ala Ile Ser Ser Tyr Asp Asp Arg Leu
            340                 345                 350

Gly His Leu Ala Pro Phe Gly Leu Arg Asp Ile Arg Asn Thr Gly Asp
        355                 360                 365
```

```
Asn Gly Ser Ala Ala Cys Asp Phe Gln Thr Val Leu Leu Val Thr Asp
    370                 375                 380
Gly Ser His Val Asn Asn Gly Ile Asn Gly Phe Leu Gln Gln Ile Thr
385                 390                 395                 400
Glu Ser Ser His Phe Met Pro Cys Asn Asn Arg Ala Leu Leu Leu His
            405                 410                 415
Cys Gln Met Glu Ser Ser Gly Ala Leu Leu Val Ala Tyr Tyr Asp His
            420                 425                 430
Asn Val Ile Asp Ser Leu Gln Thr Thr Arg Leu Leu Gln Gln Phe Gly
            435                 440                 445
His Leu Ile Lys Cys Leu Gln Ser Pro Leu Asp Leu Ser Ser Met Ala
    450                 455                 460
Glu Val Asn Leu Met Thr Glu Tyr Asp Arg Ala Glu Ile Glu Ser Trp
465                 470                 475                 480
Asn Ser Gln Pro Leu Glu Val Gln Asp Thr Leu Ile His His Glu Met
                485                 490                 495
Leu Lys Ala Val Ser His Ser Pro Thr Lys Thr Ala Ile Gln Ala Trp
            500                 505                 510
Asp Gly Asp Trp Thr Tyr Ser Glu Leu Asp Asn Val Ser Ser Arg Leu
            515                 520                 525
Ala Val His Ile Lys Ser Leu Gly Leu Arg Ala Gln Gln Ala Ile Ile
    530                 535                 540
Pro Val Tyr Phe Glu Lys Ser Lys Trp Val Ile Ala Ser Met Leu Ala
545                 550                 555                 560
Val Leu Lys Ser Gly Asn Ala Phe Thr Leu Ile Asp Pro Asn Asp Pro
                565                 570                 575
Pro Ala Arg Thr Ala Gln Val Val Thr Gln Thr Arg Ala Thr Val Ala
            580                 585                 590
Leu Thr Ser Lys Leu His Arg Glu Thr Val Gln Lys Leu Val Gly Arg
            595                 600                 605
Cys Val Val Asp Asp Glu Leu Leu Gln Ser Val Ser Ala Ser Asp
    610                 615                 620
Asp Phe Ser Ser Leu Thr Lys Ser Gln Asp Leu Ala Tyr Val Ile Phe
625                 630                 635                 640
Thr Ser Gly Ser Thr Gly Asp Pro Lys Gly Ile Met Ile Glu His Arg
                645                 650                 655
Ala Phe Ser Ser Cys Ala Leu Lys Phe Gly Ala Ser Leu Gly Ile Asn
            660                 665                 670
Ser Asp Thr Arg Ala Leu Gln Phe Gly Thr His Ala Phe Gly Ala Cys
            675                 680                 685
Leu Leu Glu Ile Met Thr Thr Leu Ile Asn Gly Gly Cys Val Cys Ile
    690                 695                 700
Pro Ser Asp Asp Arg Met Asn Ser Ile Pro Ser Phe Ile Asn Arg
705                 710                 715                 720
Tyr Asn Val Asn Trp Met Met Ala Thr Pro Ser Tyr Met Gly Thr Phe
                725                 730                 735
Ser Pro Glu Asp Val Pro Gly Leu Ala Thr Leu Val Leu Val Gly Glu
            740                 745                 750
Gln Met Ser Ser Ser Val Asn Ala Ile Trp Ala Pro Lys Leu Gln Leu
            755                 760                 765
Leu Asn Gly Tyr Gly Gln Ser Glu Ser Ser Ser Ile Cys Phe Ala Ser
    770                 775                 780
```

-continued

```
Asn Met Ser Thr Glu Pro Asn Met Gly Arg Ala Val Gly Ala His
785                 790                 795                 800

Ser Trp Val Ile Asp Pro Asn Asp Ile Asn Arg Leu Val Pro Ile Gly
                    805                 810                 815

Ala Val Gly Glu Leu Val Ile Glu Ser Pro Gly Ile Ala Arg Asp Tyr
                820                 825                 830

Ile Val Pro Pro Pro Glu Lys Ser Pro Phe Phe Thr Asp Ile Pro
            835                 840                 845

Ser Trp Tyr Pro Ala Asn Thr Phe Pro Asp Gly Ala Lys Leu Tyr Arg
850                 855                 860

Thr Gly Asp Leu Ala Arg Tyr Ala Ser Asp Gly Ser Ile Val Cys Leu
865                 870                 875                 880

Gly Arg Ile Asp Ser Gln Val Lys Ile Arg Gly Gln Arg Val Glu Leu
                885                 890                 895

Gly Ala Ile Glu Thr His Leu Arg Gln Gln Met Pro Asp Asp Leu Thr
                900                 905                 910

Ile Val Val Glu Ala Thr Lys Arg Ser Gln Ser Ala Asn Ser Thr Ser
            915                 920                 925

Leu Ile Ala Phe Leu Ile Gly Ser Ser Tyr Phe Gly Asn Arg Pro Ser
930                 935                 940

Asp Ala His Ile Leu Asp His Asp Ala Thr Lys Ala Ile Asn Ile Lys
945                 950                 955                 960

Leu Glu Gln Val Leu Pro Arg His Ser Ile Pro Ser Phe Tyr Ile Cys
                965                 970                 975

Met Leu Glu Leu Pro Arg Thr Ala Thr Gly Lys Ile Asp Arg Arg Arg
                980                 985                 990

Leu Arg Ile Met Gly Lys Asp Ile Leu Asp Lys Gln Thr Gln Gly Ala
            995                 1000                1005

Ile Val Gln Gln Ala Pro Ala Pro Ile Pro Val Phe Ala Asp Thr Ala
    1010                1015                1020

Ala Lys Leu His Ser Ile Trp Val Gln Ser Leu Gly Ile Asp Pro Ala
1025                1030                1035                1040

Thr Val Asn Val Gly Ala Thr Phe Phe Glu Leu Gly Gly Asn Ser Ile
                1045                1050                1055

Thr Ala Ile Lys Met Val Asn Met Ala Arg Ser Val Gly Met Asp Leu
                1060                1065                1070

Lys Val Ser Asn Ile Tyr Gln His Pro Thr Leu Ala Gly Ile Ser Ala
            1075                1080                1085

Val Val Lys Gly Asp Pro Leu Ser Tyr Thr Leu Ile Pro Lys Ser Thr
    1090                1095                1100

His Glu Gly Pro Val Glu Gln Ser Tyr Ser Gln Gly Arg Leu Trp Phe
1105                1110                1115                1120

Leu Asp Gln Leu Asp Val Gly Ser Leu Trp Tyr Leu Ile Pro Tyr Ala
                1125                1130                1135

Val Arg Met Arg Gly Pro Val Asn Val Asp Ala Leu Arg Arg Ala Leu
                1140                1145                1150

Ala Ala Leu Glu Gln Arg His Glu Thr Leu Arg Thr Thr Phe Glu Asp
            1155                1160                1165

Gln Asp Gly Val Gly Val Gln Ile Val His Glu Lys Leu Ser Glu Glu
    1170                1175                1180

Met Lys Val Ile Asp Leu Cys Gly Ser Asp Leu Asp Pro Phe Glu Val
1185                1190                1195                1200

Leu Asn Gln Glu Gln Thr Thr Pro Phe Asn Leu Ser Ser Glu Ala Gly
```

-continued

```
                 1205                1210                1215
Trp Arg Ala Thr Leu Leu Arg Leu Gly Glu Asp Asp His Ile Leu Thr
            1220                1225                1230
Ile Val Met His His Ile Ile Ser Asp Gly Trp Ser Ile Asp Val Leu
            1235                1240                1245
Arg Arg Asp Leu Asn Gln Leu Tyr Ser Ala Ala Leu Lys Asp Ser Lys
            1250                1255                1260
Asp Pro Leu Ser Ala Leu Thr Pro Leu Pro Ile Gln Tyr Ser Asp Phe
1265                1270                1275                1280
Ala Lys Trp Gln Lys Asp Gln Phe Ile Glu Gln Glu Lys Gln Leu Asn
            1285                1290                1295
Tyr Trp Lys Lys Gln Leu Lys Asp Ser Ser Pro Ala Lys Ile Pro Thr
            1300                1305                1310
Asp Phe Ala Arg Pro Ala Leu Leu Ser Gly Asp Ala Gly Cys Val His
            1315                1320                1325
Val Thr Ile Asp Gly Glu Leu Tyr Gln Ser Leu Arg Ala Phe Cys Asn
            1330                1335                1340
Glu His Asn Thr Thr Ser Phe Val Val Leu Leu Ala Ala Phe Arg Ala
1345                1350                1355                1360
Ala His Tyr Arg Leu Thr Ala Val Glu Asp Ala Val Ile Gly Thr Pro
            1365                1370                1375
Ile Ala Asn Arg Asn Arg Pro Glu Leu Glu Asp Ile Ile Gly Cys Phe
            1380                1385                1390
Val Asn Thr Gln Cys Met Arg Ile Asn Ile Asp His Asp Thr Phe
            1395                1400                1405
Gly Thr Leu Ile Asn Gln Val Lys Ala Thr Thr Thr Ala Ala Phe Glu
            1410                1415                1420
Asn Glu Asp Ile Pro Phe Glu Arg Val Val Ser Ala Leu Gln Pro Gly
1425                1430                1435                1440
Ser Arg Asp Leu Ser Ser Thr Pro Leu Ala Gln Leu Ile Phe Ala Val
            1445                1450                1455
His Ser Gln Lys Asp Leu Gly Arg Phe Lys Phe Gln Gly Leu Glu Ser
            1460                1465                1470
Val Pro Val Pro Ser Lys Ala Tyr Thr Arg Phe Asp Met Glu Phe His
            1475                1480                1485
Leu Phe Gln Glu Thr Asp Ser Leu Lys Gly Ser Val Asn Phe Ala Asp
            1490                1495                1500
Glu Leu Phe Lys Met Glu Thr Val Glu Asn Val Val Arg Val Phe Phe
1505                1510                1515                1520
Glu Ile Leu Arg Asn Gly Leu Gln Ser Ser Arg Thr Pro Val Ser Ile
            1525                1530                1535
Leu Pro Leu Thr Asp Gly Ile Val Thr Leu Glu Lys Leu Asp Val Leu
            1540                1545                1550
Asn Val Lys His Val Asp Tyr Pro Arg Glu Ser Ser Leu Ala Asp Val
            1555                1560                1565
Phe Gln Thr Gln Val Ser Ala Tyr Pro Asp Ser Leu Ala Val Val Asp
1570                1575                1580
Ser Ser Cys Arg Leu Thr Tyr Thr Glu Leu Asp Arg Gln Ser Asp Ile
1585                1590                1595                1600
Leu Ala Gly Trp Leu Arg Arg Arg Ser Met Pro Ala Glu Thr Leu Val
            1605                1610                1615
Ala Val Phe Ala Pro Arg Ser Cys Glu Thr Ile Val Ala Phe Phe Gly
            1620                1625                1630
```

-continued

Val Leu Lys Ala Asn Leu Ala Tyr Leu Pro Leu Asp Val Arg Ser Pro
            1635                1640                1645

Ser Ala Arg Val Gln Asp Ile Leu Ser Gly Leu Ser Gly Pro Thr Ile
        1650                1655                1660

Val Leu Ile Gly His Asp Thr Ala Pro Pro Asp Ile Glu Val Thr Asn
1665                1670                1675                1680

Val Glu Phe Val Arg Ile Arg Asp Ala Leu Asn Asp Ser Asn Ala Asp
            1685                1690                1695

Gly Phe Glu Val Ile Glu His Asp Ser Thr Lys Pro Ser Ala Thr Ser
            1700                1705                1710

Leu Ala Tyr Val Leu Tyr Thr Ser Gly Ser Thr Gly Arg Pro Lys Gly
            1715                1720                1725

Val Met Ile Glu His Arg Val Ile Ile Arg Thr Val Thr Ser Gly Cys
            1730                1735                1740

Ile Pro Asn Tyr Pro Ser Glu Thr Arg Met Ala His Met Ala Thr Ile
1745                1750                1755                1760

Ala Phe Asp Gly Ala Ser Tyr Glu Ile Tyr Ser Ala Leu Leu Phe Gly
            1765                1770                1775

Arg Thr Leu Val Cys Val Asp Tyr Met Thr Thr Leu Asp Ala Arg Ala
            1780                1785                1790

Leu Lys Asp Val Phe Phe Arg Glu His Val Asn Ala Ala Ser His Val
            1795                1800                1805

Thr Ser Ser Ser Gln Asp Val Pro Leu Arg Val Pro Arg Arg Leu Ser
            1810                1815                1820

Arg Thr Leu Met Phe Phe Phe Leu Val Val Thr Asp Ser Thr Ala Pro
1825                1830                1835                1840

Asp Ala Leu Asp Ala Gln Gly Leu Tyr Gln Gly Val Gln Cys Tyr Asn
            1845                1850                1855

Gly Tyr Gly Pro Thr Glu Asn Gly Val Met Ser Thr Ile Tyr Pro Ile
            1860                1865                1870

Asp Ser Thr Glu Ser Phe Ile Asn Gly Val Pro Ile Gly Arg Ala Leu
            1875                1880                1885

Asn Asn Ser Gly Ala Tyr Val Val Asp Pro Glu Gln Gln Leu Val Gly
            1890                1895                1900

Ile Gly Val Met Gly Glu Leu Val Val Thr Gly Asp Gly Leu Ala Arg
1905                1910                1915                1920

Gly Tyr Ser Asp Lys Ala Leu Asp Glu Asn Arg Phe Val His Ile Thr
            1925                1930                1935

Val Asn Asp Gln Thr Val Lys Ala Tyr Arg Thr Gly Asp Arg Val Arg
            1940                1945                1950

Tyr Arg Ile Gly Asp Gly Leu Ile Glu Phe Phe Gly Arg Met Asp Thr
            1955                1960                1965

Gln Phe Lys Ile Arg Gly Asn Arg Ile Glu Ser Ala Glu Ile Glu Ala
            1970                1975                1980

Ala Leu Leu Arg Asp Ser Ser Val Arg Asp Ala Ala Val Val Leu Gln
1985                1990                1995                2000

Gln Asn Glu Asp Gln Ala Pro Glu Ile Leu Gly Phe Val Ala Asp
            2005                2010                2015

His Asp His Ser Glu Asn Asp Lys Gly Gln Ser Ala Asn Gln Val Glu
            2020                2025                2030

Gly Trp Gln Asp His Phe Glu Ser Gly Met Tyr Ser Asp Ile Gly Glu
            2035                2040                2045

-continued

```
Ile Asp Pro Ser Thr Ile Gly Ser Asp Phe Lys Gly Trp Thr Ser Met
2050                2055                2060

Tyr Asp Gly Ser Gln Ile Asp Phe Asp Glu Met His Glu Trp Leu Gly
2065                2070                2075                2080

Glu Thr Thr Arg Thr Leu His Asp Asn Arg Ser Leu Gly Asn Val Leu
            2085                2090                2095

Glu Ile Gly Thr Gly Ser Gly Met Ile Leu Phe Asn Leu Asp Ser Arg
        2100                2105                2110

Leu Glu Ser Tyr Val Gly Leu Glu Pro Ser Arg Ser Ala Ala Ala Phe
            2115                2120                2125

Val Asn Lys Ala Thr Glu Ser Ile Pro Ser Leu Ala Gly Lys Ala Lys
        2130                2135                2140

Val Gln Val Gly Thr Ala Thr Asp Ile Gly Gln Val Asp Asp Leu His
2145                2150                2155                2160

Pro Asp Leu Val Val Leu Asn Ser Val Ile Gln Tyr Phe Pro Ser Ser
            2165                2170                2175

Glu Tyr Leu Ala Glu Ile Ala Asp Thr Leu Ile His Leu Pro Asn Val
        2180                2185                2190

Gln Arg Ile Phe Phe Gly Asp Val Arg Ser Gln Ala Thr Asn Glu His
    2195                2200                2205

Phe Leu Ala Ala Arg Ala Ile His Thr Leu Gly Lys Asn Ala Thr Lys
2210                2215                2220

Asp Asp Val Arg Gln Lys Met Ala Glu Leu Glu Asp Met Glu Glu Glu
2225                2230                2235                2240

Leu Leu Val Glu Pro Ala Phe Phe Thr Ser Leu Lys Asp Arg Phe Pro
            2245                2250                2255

Gly Leu Val Glu His Val Glu Ile Leu Pro Lys Asn Met Glu Ala Val
        2260                2265                2270

Asn Glu Leu Ser Ala Tyr Arg Tyr Ala Ala Val Val His Val Arg Gly
    2275                2280                2285

Ser Leu Gly Asp Glu Leu Val Leu Pro Val Glu Lys Asp Asp Trp Ile
2290                2295                2300

Asp Phe Gln Ala Asn Gln Leu Asn Gln Lys Ser Leu Gly Asp Leu Leu
2305                2310                2315                2320

Lys Ser Ser Asp Ala Ala Ile Met Ala Val Ser Lys Ile Pro Phe Glu
            2325                2330                2335

Ile Thr Ala Phe Glu Arg Gln Val Val Ala Ser Leu Asn Ser Asn Ile
        2340                2345                2350

Asp Glu Trp Gln Leu Ser Thr Ile Arg Ser Ser Ala Glu Gly Asp Ser
    2355                2360                2365

Ser Leu Ser Val Pro Asp Ile Phe Arg Ile Ala Gly Glu Ala Gly Phe
2370                2375                2380

Arg Val Glu Val Ser Ser Ala Arg Gln Trp Ser Gln Asn Gly Ala Leu
2385                2390                2395                2400

Asp Ala Val Phe His His Cys Cys Ser Gln Gly Arg Thr Leu Val Asn
            2405                2410                2415

Phe Pro Thr Asp His His Leu Arg Gly Ser Asp Leu Leu Thr Asn Arg
        2420                2425                2430

Pro Leu Gln Arg Leu Gln Asn Arg Arg Ile Ala Ile Glu Val Arg Glu
    2435                2440                2445

Arg Leu Arg Ser Leu Leu Pro Ser Tyr Met Ile Pro Ser Asn Ile Val
2450                2455                2460

Val Leu Asp Lys Met Pro Leu Asn Ala Asn Gly Lys Val Asp Arg Lys
```

```
                    2465                2470                2475                2480
Glu Leu Ser Arg Arg Ala Lys Val Val Pro Lys Gln Gln Thr Ala Ala
                2485                2490                2495
Pro Leu Pro Thr Phe Pro Ile Ser Glu Val Glu Val Ile Leu Cys Glu
            2500                2505                2510
Glu Ala Thr Glu Val Phe Gly Met Lys Val Asp Ile Thr Asp His Phe
            2515                2520                2525
Phe Asn Leu Gly Gly His Ser Leu Leu Ala Thr Lys Leu Ile Ser Arg
            2530                2535                2540
Ile Asp Gln Arg Leu Lys Val Arg Ile Thr Val Lys Asp Val Phe Asp
2545                2550                2555                2560
His Pro Val Phe Ala Asp Leu Ala Ser Val Ile Arg Gln Gly Leu Gly
            2565                2570                2575
Leu Gln Gln Pro Val Ser Asp Gly Gln Gly Gln Asp Arg Ser Ala His
            2580                2585                2590
Met Ala Pro Arg Thr Glu Thr Glu Ala Ile Leu Cys Asp Glu Phe Ala
            2595                2600                2605
Lys Val Leu Gly Phe Gln Val Gly Ile Thr Asp Asn Phe Phe Asp Leu
            2610                2615                2620
Gly Gly His Ser Leu Met Ala Thr Lys Leu Ala Val Arg Ile Gly His
2625                2630                2635                2640
Arg Leu Asp Thr Thr Val Ser Val Lys Asp Val Phe Asp His Pro Val
                2645                2650                2655
Leu Phe Gln Leu Ala Ile Ala Leu Asp Asn Leu Val Gln Ser Lys Thr
            2660                2665                2670
Asn Glu Ile Val Gly Gly Arg Glu Met Ala Glu Tyr Ser Pro Phe Gln
            2675                2680                2685
Leu Leu Phe Thr Glu Asp Pro Glu Glu Phe Met Ala Ser Glu Ile Lys
            2690                2695                2700
Pro Gln Leu Glu Leu Gln Glu Ile Ile Gln Asp Ile Tyr Pro Ser Thr
2705                2710                2715                2720
Gln Met Gln Lys Ala Phe Leu Phe Asp His Thr Thr Ala Arg Pro Arg
                2725                2730                2735
Pro Phe Val Pro Phe Tyr Ile Asp Phe Pro Ser Thr Ser Glu Pro Asp
            2740                2745                2750
Ala Ala Gly Leu Ile Lys Ala Cys Glu Ser Leu Val Asn His Leu Asp
            2755                2760                2765
Ile Phe Arg Thr Val Phe Ala Glu Ala Ser Gly Glu Leu Tyr Gln Val
            2770                2775                2780
Val Leu Ser Cys Leu Asp Leu Pro Ile Gln Val Ile Glu Thr Glu Asp
2785                2790                2795                2800
Asn Ile Asn Thr Ala Thr Asn Glu Phe Leu Asp Glu Phe Ala Lys Glu
                2805                2810                2815
Pro Val Arg Leu Gly His Pro Leu Ile Arg Phe Thr Ile Ile Lys Gln
            2820                2825                2830
Thr Lys Ser Met Arg Val Ile Met Arg Ile Ser His Ala Leu Tyr Asp
            2835                2840                2845
Gly Leu Ser Leu Glu His Val Val Arg Lys Leu His Met Leu Tyr Asn
            2850                2855                2860
Gly Arg Ser Leu Leu Pro Pro His Gln Phe Ser Arg Tyr Met Gln Tyr
2865                2870                2875                2880
Thr Ala Asp Gly Arg Glu Ser Gly His Gly Phe Trp Arg Asp Val Ile
                2885                2890                2895
```

```
Gln Asn Thr Pro Met Thr Ile Leu Ser Asp Asp Thr Val Val Asp Gly
            2900                2905                2910

Asn Asp Ala Thr Cys Lys Ala Leu His Leu Ser Lys Ile Val Asn Ile
            2915                2920                2925

Pro Ser Gln Val Leu Arg Gly Ser Ser Asn Ile Ile Thr Gln Ala Thr
            2930                2935                2940

Val Phe Asn Ala Ala Cys Ala Leu Val Leu Ser Arg Glu Ser Asp Ser
2945                2950                2955                2960

Lys Asp Val Val Phe Gly Arg Ile Val Ser Gly Arg Gln Gly Leu Pro
            2965                2970                2975

Val Glu Tyr Gln Asp Ile Val Gly Pro Cys Thr Asn Ala Val Pro Val
            2980                2985                2990

Arg Ala His Ile Glu Ser Ser Asp Tyr Asn Gln Leu Leu His Asp Ile
            2995                3000                3005

Gln Asp Gln Tyr Leu Leu Ser Leu Pro His Glu Thr Ile Gly Phe Ser
            3010                3015                3020

Asp Leu Lys Arg Asn Cys Thr Asp Trp Pro Glu Ala Ile Thr Asn Phe
3025                3030                3035                3040

Ser Cys Cys Ile Thr Tyr His Asn Phe Glu Tyr His Pro Glu Ser Gln
            3045                3050                3055

Phe Glu Gln Gln Arg Val Glu Met Gly Val Leu Thr Lys Phe Val Asn
            3060                3065                3070

Ile Glu Met Asp Glu Pro Leu Tyr Asp Leu Ala Ile Ala Gly Glu Val
            3075                3080                3085

Glu Pro Asp Gly Ala Gly Leu Lys Val Thr Val Ile Ala Lys Thr Gln
            3090                3095                3100

Leu Phe Gly Arg Lys Arg Val Glu His Leu Leu Glu Glu Val Ser Lys
3105                3110                3115                3120

Thr Phe Glu Gly Leu Asn Ser Ser Leu
                3125

<210> SEQ ID NO 3
<211> LENGTH: 23
<212> TYPE: DNA
<213> ORGANISM: Fusarium

<400> SEQUENCE: 3
aattgattcg cttgaaagtc gat                                          23

<210> SEQ ID NO 4
<211> LENGTH: 25
<212> TYPE: DNA
<213> ORGANISM: Fusarium

<400> SEQUENCE: 4
cttgagagtt acgttggtct tgaac                                        25
```

What is claimed is:

1. A method for producing a secreted heterologous polypeptide, comprising:

(a) cultivating a mutant cell of a parent *Fusarium venenatum* cell under conditions conducive for the production of the secreted heterologous polypeptide, wherein (i) the mutant cell comprises a first nucleic acid encoding the secreted heterologous polypeptide, and (ii) the mutant cell comprises a second nucleic acid which comprises a disruption or a deletion in a cyclohexadepsipeptide synthetase gene, wherein the mutant cell produces less cyclohexadepsipeptide than the parent *Fusarium venenatum* cell when cultured under the same conditions as a result of the disruption or the deletion in the cyclohexadepsipeptide synthetase gene, wherein the cyclohexadepsipeptide synthetase gene encodes a cyclohexadepsipeptide synthetase having an amino acid sequence which has at least 95% identity with SEQ ID NO: 2; or a cyclohexadepsipeptide synthetase which is encoded by a nucleic acid which hybridizes under at least high stringency conditions with (i) the nucleic acid of SEQ ID NO: 1, (ii) the cDNA of SEQ ID NO: 1, or (iii) a complete complementary strand of (i) or (ii), wherein high stringency conditions are defined as prehybridization and hybridization at 45° C. in 5×SSPE, 0.3% SDS, 2001 g/ml sheared and denatured salmon sperm DNA, and 50% formamide and washing three times each for 15 minutes using 2×SSC, 0.2% SDS at 55° C.; and (b) isolating the secreted heterologous polypeptide from the cultivation medium.

2. The method of claim 1, wherein the *Fusarium venenatum* cell is *Fusarium venenatum* ATCC 20334.

3. The method of claim 1, wherein the *Fusarium venenatum* cell is a morphological mutant.

4. The method of claim 3, wherein the *Fusarium venenatum* cell is a morphological mutant of *Fusarium venenatum* ATCC 20334.

5. The method of claim 1, wherein the cyclohexadepsipeptide synthetase gene encodes the cyclohexadepsipeptide synthetase of SEQ ID NO: 2.

6. The method of claim 5, wherein the cyclohexadepsipeptide synthetase gene has the nucleic acid sequence of SEQ ID NO: 1.

7. The method of claim 1, wherein the mutant cell produces at least 25% less of the cyclohexadepsipeptide than the parent *Fusarium venenatum* cell when cultured under identical conditions.

8. The method of claim 1, wherein the mutant cell produces no cyclohexadepsipeptide.

9. The method of claim 1, wherein the mutant cell comprises at least two copies of the first nucleic acid.

10. The method of claim 1, wherein the secreted heterologous polypeptide is a hormone, enzyme, receptor or portion thereof, antibody or portion thereof, or reporter.

11. The method of claim 10, wherein the enzyme is an oxidoreductase, transferase, hydrolase, lyase, isomerase, or ligase.

12. The method of claim 1, wherein the mutant cell further comprises one or more nucleic acids, in addition to the two nucleic acids already present in the mutant cell, which comprise a disruption or a deletion to reduce or eliminate expression of the one or more additional nucleic acids.

13. The method of claim 12, wherein the third nucleic acid encodes an enzyme selected from the group consisting of an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, and xylanase.

14. The method of claim 12, wherein a third nucleic acid encodes a protease.

15. A cyclohexadepsipeptide-deficient mutant cell of a parent *Fusarium venenatum* cell, comprising (i) a first nucleic acid encoding a secreted heterologous polypeptide, and (ii) a second nucleic acid comprising a disruption or a deletion in a cyclohexadepsipeptide synthetase gene, wherein the *Fusarium venenatum* mutant cell produces less cyclohexadepsipeptide than the parent *Fusarium venenatum* cell when cultured under the same conditions as a result of the disruption or the deletion in the cyclohexadepsipeptide synthetase gene, wherein the cyclohexadepsipeptide synthetase gene encodes a cyclohexadepsipeptide synthetase having an amino acid sequence which has at least 95% identity with SEQ ID NO: 2; or a cyclohexadepsipeptide synthetase which is encoded by a nucleic acid which hybridizes under at least high stringency conditions with (i) the nucleic acid of SEQ ID NO: 1, (ii) the cDNA of SEQ ID NO: 1, or (iii) a complete complementary strand of (i) or (ii), wherein high stringency conditions are defined as prehybridization and hybridization at 45° C. in 5×SSPE, 0.3% SDS, 200 µg/ml sheared and denatured salmon sperm DNA, and 50% formamide and washing three times each for 15 minutes using 2×SSC, 0.2% SDS at 55° C.

16. The mutant cell of claim 15, wherein the *Fusarium venenatum* cell is *Fusarium venenatum* ATCC 20334.

17. The mutant cell of claim 15, wherein the *Fusarium venenatum* cell is a morphological mutant.

18. The mutant cell of claim 17, wherein the *Fusarium venenatum* cell is a morphological mutant of *Fusarium venenatum* ATCC 20334.

19. The mutant cell of claim 15, wherein the cyclohexadepsipeptide synthetase gene encodes the cyclohexadepsipeptide synthetase of SEQ ID NO: 2.

20. The mutant cell of claim 19, wherein the cyclohexadepsipeptide synthetase gene has the nucleic acid sequence of SEQ ID NO: 1.

21. The mutant cell of claim 15, which comprises at least two copies of the first nucleic acid.

22. The mutant cell of claim 15, wherein the secreted heterologous polypeptide is a hormone, enzyme, receptor or portion thereof, antibody or portion thereof, or reporter.

23. The mutant cell of claim 22, wherein the enzyme is an oxidoreductase, transferase, hydrolase, lyase, Isomerase, or ligase.

24. The mutant cell of claim 15, wherein the mutant cell further comprises one or more nucleic acids, in addition to the two nucleic acids already present in the mutant cell, which comprise a disruption or a deletion to reduce or eliminate expression of the one or more additional nucleic adds.

25. The mutant cell of claim 24, wherein the third nucleic acid encodes an enzyme selected from the group consisting of an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, and xylanase.

26. The method of claim 1, wherein the cyclohexadepsipeptide synthetase gene encodes a cyclohexadepsipeptide synthetase having an amino acid sequence which has at least 95% identity with SEQ ID NO: 2.

27. The method of claim 1, wherein the cyclohexadepsipeptide synthetase is encoded by a nucleic acid which hybridizes under at least high stringency conditions with (i) the nucleic acid of SEQ ID NO: 1, (ii) the cDNA of SEQ ID NO: 1, or (iii) a complete complementary strand of (I) or (ii), wherein high stringency conditions are defined as prehybridization and hybridization at 45° C. in 5×SSPE, 0.3% SDS 200 µg/ml sheared and denatured salmon sperm DNA, and 50% formamide and washing three times each for 15 minutes using 2×SSC, 0.2% SDS at 65° C.

28. The mutant cell of claim 15, wherein the cyclohexadepsipeptide synthetase gene encodes a cyclohexadepsipeptide synthetase having an amino acid sequence which has at least 95% identity with SEQ ID NO: 2.

29. The mutant cell of claim 15, wherein the cyclohexadepsipeptide synthetase is encoded by a nucleic acid which hybridizes under at least high stringency conditions with (i) the nucleic acid of SEQ ID NO: 1, (ii) the cDNA of SEQ ID NO: 1, or (iii) a complete complementary strand of (i) or (ii), wherein high stringency conditions are defined as prehybridization and hybridization at 45° C. in 5×SSPE, 0.3% SDS, 200 µg/ml sheared and denatured salmon sperm DNA, and 50% formamide and washing three times each for 15 minutes using 2×SSC, 0.2% SDS at 65° C.

* * * * *